United States Patent
Budunova et al.

(10) Patent No.: US 10,799,475 B2
(45) Date of Patent: Oct. 13, 2020

(54) SUBSTITUTED PHENYL AZIRIDINE PRECURSOR ANALOGS FOR INHIBITING ANDROGEN-INDEPENDENT PROSTATE CANCER CELL GROWTH

(71) Applicant: Northwestern University, Evanston, IL (US)

(72) Inventors: Irina Budunova, Chicago, IL (US); Alexander Yemelyanov, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/059,771

(22) Filed: Aug. 9, 2018

(65) Prior Publication Data
US 2018/0344691 A1    Dec. 6, 2018

Related U.S. Application Data

(63) Continuation of application No. 15/487,036, filed on Apr. 13, 2017, now abandoned, which is a continuation of application No. 14/963,788, filed on Dec. 9, 2015, now abandoned, which is a continuation of application No. 14/057,518, filed on Oct. 18, 2013, now abandoned, which is a continuation of application No. 12/335,911, filed on Dec. 16, 2008, now abandoned.

(60) Provisional application No. 61/014,225, filed on Dec. 17, 2007.

(51) Int. Cl.
| | |
|---|---|
| *A61K 31/396* | (2006.01) |
| *A61K 31/135* | (2006.01) |
| *A61K 31/216* | (2006.01) |
| *C07C 229/38* | (2006.01) |
| *A61K 31/222* | (2006.01) |
| *A61K 45/06* | (2006.01) |
| *C12Q 1/6886* | (2018.01) |
| *G01N 33/574* | (2006.01) |

(52) U.S. Cl.
CPC .......... *A61K 31/396* (2013.01); *A61K 31/135* (2013.01); *A61K 31/216* (2013.01); *A61K 31/222* (2013.01); *A61K 45/06* (2013.01); *C07C 229/38* (2013.01); *C12Q 1/6886* (2013.01); *G01N 33/57434* (2013.01); *C12Q 2600/158* (2013.01)

(58) Field of Classification Search
CPC .. A61K 31/216; A61K 31/135; A61K 31/137; A61K 31/396
See application file for complete search history.

(56) References Cited

U.S. PATENT DOCUMENTS

| | | | | |
|---|---|---|---|---|
| 2003/0049645 | A1* | 3/2003 | Mu | C12N 9/6454 435/6.16 |
| 2003/0055030 | A1 | 3/2003 | De Bosscher et al. | |
| 2006/0276527 | A1* | 12/2006 | Tidmarsh | A61K 31/11 514/406 |

FOREIGN PATENT DOCUMENTS

WO    0145693    6/2001

OTHER PUBLICATIONS

Bullock et al., "Emerging drug theraptics for benign prostatic hyperplasia", Expert Opinion Emerging Drugs, 2006, 11(1):111-123.
Chebotaev et al., "The Mechanisms of Tumor Suppressor Effect of Glucocorticoid Receptor in Skin", Molecular Carcinogenesis, 2007, 46: 732-740.
Clarke et al., "Pharmacologic Modulation of Sebaceous Gland Activity: Mechanisms and Clinical Applications", Dermatologic Clinics, 2007, 25:137-146.
De Bosscher et al., "A fully dissociated compound of plant origin for inflammatory gene repression", PNAS, Nov. 1, 2005, 102(44):15827-15832.
De Bosscher et al., "The Interplay between the Glucocorticoid Receptor and Nuclear Factor-KB or Activator Protein-1: Molecular Mechanisms for Gene Repression", Endocrine Reviews, 2003, 24(4):488-522.
Dondi et al., "Expression and role of functional glucocorticoid receptors in the human androgen-independent prostate cancer cell line, DU145", Journal of Molecular Endocrinology, 2001, 26:185-191.
Feldman et al., "The Development of Androgen-Independent Prostate Cancer", Nature, Oct. 2001, 1:34-45.
Haverkamp et al., "Prostate Inflammation and Its Potential Impact on Prostate Cancer: A Current Review", Journal of Cellular Biochemistry, 2008, 103:1344-1353.
Heinlein et al., "Androgen Receptor in Prostate Cancer", Endocrine Reviews, 2004, 25(2):2746-308.
Johnson et al., British J. of Cancer, 2001, 84(10:1424-1431.
Kaufman, "Androgens and alopecia", Molecular and Cellular Endocrinology, 2002, 198:89-95.
Kramer et al., "Is Benign Prostatic Hyperplasia (BPH) an Immune Inflammatory Disease?", European Urology, 2007, 51:1202-1216.

(Continued)

*Primary Examiner* — James D. Anderson
(74) *Attorney, Agent, or Firm* — Quarles & Brady LLP

(57) ABSTRACT

Disclosed are methods and pharmaceutical compositions for modulating one or more steroidal receptor activities. The methods typically utilize and the pharmaceutical compositions typically include one or more substituted phenyl aziridine precursors, their respective aziridines, analogs thereof, derivatives thereof, or pharmaceutically acceptable salts thereof such as CpdA. The methods and compositions may be used for treating diseases, disorders, and conditions associated with glucocorticoid receptor activity, androgen receptor activity, or both, such as cancers, acne vulgaris, and alopecia.

10 Claims, 10 Drawing Sheets

(56) References Cited

OTHER PUBLICATIONS

Lee et al., "In vivo and in vitro approaches to study metastasis in human prostatic cancer", Cancer and Metastasis Reviews, 1993, 12:21-28.
Louw et al., "Mechanism for the Stabilization in Vivo of the Aziridine Precursor 2-(4-Acetoxyphenyl)-2-chloro-N-methyl-ethylammonium Chloride by Serum Proteins", Biochemical Pharmacology, 1997, 53:189-197.
Louw et al., "Salsola tuberculatiformis Botschantzev and an Aziridine Precursor Analog Mediate the in Vivo Increase in Free Corticosterone and Decrease in Corticosteroid-Binding Globulin in Female Wistar Rats", Endocrinology, 1999, 140(5):2044-2053.
Louw et al., Influence of an Aziridine Precursor on the In Vitro Binding Parameters of Rat and Ovine Corticosteroid-Binding Globulin (CBG), Biochemical Pharmacology, 2000, 59:167-175.
Mahe et al., "Androgenic alopecia and microinflammation", International Journal of Dermatology, 2000, 39:576-584.
McKay et al., "Molecular Control of Immune/Inflammatory Responses: Interactions Between Nuclear Factor-KB and Steroid Receptor-Signaling Pathways", Endocrine Reviews, 1999, 20(4):435-459.
Nelius et al., "Androgen receptor targets NFjB and TSP1 to suppress prostate tumor growth in vivo", International Journal of Cancer, Sep. 1, 2007, 121(5):999-1008.
Nelson, "Prostate Cancer Prevention", Current Opinion in Urology, 2007, 17:157-167.
Nishimura et al., "Potential Mechanism for the Effects of Dexamethasone on Growth of Androgen-Independent Prostate Cancer", Journal of the National Cancer Institute: Nov. 21, 2001, 93(22):1739-1746.
Saika et al., International Journal of Urology, 2001, 8:290-294.
Sausville et al., Cancer Research, 2006, 66:3351-3354.
Schacke et al., "Selective glucocorticoid receptor agonists (SEGRAs): Novel ligands with an improved therapeutic index", Molecular and Cellular Endocrinology, 2007, 275:109-117.
Smith et al., "Mechanism of the Glucocorticoid Regulation of Growth of the Androgen-sensitive Prostate-derived R3327H-G8-A1 Tumor Cell Line", Journal of Biological Chemistry, Oct. 15, 1985, 260(23):12454-12463.
Sutcliffe et al., "Inflammation in the etiology of prostate cancer: An epidemiologic perspective", Urologic Oncology: Seminars and Original Investigations, 2007, 25:242-249.
Tanner et al., "Anti-androgenic properties of Compound A, an analog of a non-steroidal plant compound", Molecular and Cellular Endocrinology, 2003, 201:155-164.
Trueb, "Is Androgenetic Alopecia a Photoaggravated Dermatosis?", Dermatology, 2003, 207:343-348.
Van Der Merwe et al., "The application of mass spectrometry in the study of labile natural products", Biochemical Society Transactions, 1991, Biochem Soc Trans 19:432s.
Yano et al., "Glucocorticoids Suppress Tumor Lymphangiogenesis of Prostate Cancer Cells", Human Cancer Biology, Oct. 15, 2006, 12(20):6012-6017.
Yemelyanov et al., "Tumor suppressor activity of glucocorticoid receptor in the prostate", Oncogene, 2007, 26:1885-1896.
Yemelyanov et al., "Novel Steroid Receptor Phyto-Modulator Compound A Inhibits Growth and Survival of Prostate Cancer Cells", Cancer Research, Jun. 15, 2008, 68(12):4763-4773.
Adcock IM. Glucocorticoid-regulated transcription factors. Pulmonary pharmacology & therapeutics. 2001; 14:211-219.
Baida G, Bhalla P, Kirsanov K, Lesovaya E, Yakubovskaya M, Yuen K, Guo S, Lavker RM, Readhead B, Dudley JT, Budunova I. REDD1 functions at the crossroads between the therapeutic and adverse effects of topical glucocorticoids. EMBO Mol Med. 2015; 7:42-58.
Barnes PJ. Achieving asthma control. Curr Med Res Opin. 2005; 21:S5-9.
Barnes PJ. Anti-inflammatory actions of glucocorticoids: molecular mechanisms. Clinical science. 1998; 94:557-572.
Barnes PJ. Corticosteroid effects on cell signalling. Eur Respir J. 2006; 27:413-426.

Barnes PJ. Glucocorticosteroids: current and future directions. British journal of pharmacology. 2011; 163:29-43.
Basson PA, et al. "Grootlamsiekte", a specific syndrome of prolonged gestation in sheep caused by a shrub *Salsola tuberculata* (*Fenzl ex Moq*) *Schinz* var. *tomentosa* C. A. Smith ex Aellen. The Onderstepoort journal of veterinary research. 1969; 36:59-103.
Beato M, Herrlich P, Schutz G. Steroid hormone receptors: many actors in search of a plot. Cell. 1995; 83:851-857.
Beck IM,, et al. Compound A, a selective glucocorticoid receptor modulator, enhances heat shock protein Hsp70 gene promoter activation. PloS one. 2013; 8:e69115.
Botschantzev V. A synopsis of Salsola (*Chenopodiaceae*) from South and South-West Africa. Kew Bulletin. 1974; 29:597-614.
Britto FA, Begue G, Rossano B, Docquier A, Vernus B, Sar C, Ferry A, Bonnieu A, Ollendorff V, Favier FB. REDD1 deletion prevents dexamethasone-induced skeletal muscle atrophy. Am J Physiol Endocrinol Metab. 2014; 307:E983-993.
Buckingham JC. Glucocorticoids: exemplars of multi-tasking. British journal of pharmacology. 2006; 147:S258-268.
Buda G, et al. Bortezomib with thalidomide plus dexamethasone compared with thalidomide plus doxorubicin and dexamethasone as induction therapy in previously untreated multiple myeloma patients. Acta haematologica. 2013; 129:35-39.
Budunova IV, et al. Glucocorticoid receptor functions as a potent suppressor of mouse skin carcinogenesis. Oncogene. 2003; 22:3279-3287.
Chebotaev D, et al. The mechanisms of tumor suppressor effect of glucocorticoid receptor in skin. Molecular carcinogenesis. 2007; 46:732-740.
Chebotaev D, et al. The tumor suppressor effect of the glucocorticoid receptor in skin is mediated via its effect on follicular epithelial stem cells. Oncogene. 2007; 26:3060-3068.
Chun E, Lee HS, Bang BR, Kim TW, Lee SH, Kim JH, Cho SH, Min Ku, Kim YY, Park HW. Dexamethasone-induced FKBP51 expression in peripheral blood mononuclear cells could play a role in predicting the response of asthmatics to treatment with corticosteroids. Journal of clinical immunology. 2011; 31:122-127.
Davies TH, Ning YM, Sanchez ER. A new first step in activation of steroid receptors: hormone-induced switching of FKBP51 and FKBP52 immunophilins. The Journal of biological chemistry. 2002; 277:4597-4600.
De Bosscher K, et al. Selective modulation of the glucocorticoid receptor can distinguish between transrepression of NF-kappaB and AP-1. Cell Mol Life Sci. 2014; 71:143-163.
De Bosscher K, et al. Classic glucocorticoids versus non-steroidal glucocorticoid receptor modulators: survival of the fittest regulator of the immune system? Brain Behav Immun. 2010; 24:1035-1042.
De Bosscher K. Selective Glucocorticoid Receptor modulators. The Journal of steroid biochemistry and molecular biology. 2010; 120:96-104.
De Bosscher K, et al. A fully dissociated compound of plant origin for inflammatory gene repression. Proceedings of the National Academy of Sciences of the United States of America. 2005; 102:15827-15832.
De Bosscher K, Van den Berghe W, Haegeman G. Cross-talk between nuclear receptors and nuclear factor kappaB. Oncogene. 2006; 25:6868-6886.
De Bosscher K, et al. The interplay between the glucocorticoid receptor and nuclear factor-kappaB or activator protein-1: molecular mechanisms for gene repression. Endocrine reviews. 2003; 24:488-522.
De Lange M. Prolonged gestation in karakul ewes in South West Africa. Proc 4th Internat Congress Anim Reprod The Hague. 1961; 3:590-592.
Dewint P, et al. A plant-derived ligand favoring monomeric glucocorticoid receptor conformation with impaired transactivation potential attenuates collagen-induced arthritis. Journal of immunology. 2008; 180:2608-2615.
Gibbs GE, et al. List of species of southern African plants, Ed. 2, Part 2. Memoirs of the Botanical Survey of South Africa. 1987; 56.
Gossye V, et al. Differential mechanism of NF-kappaB inhibition by two glucocorticoid receptor modulators in rheumatoid arthritis synovial fibroblasts. Arthritis and rheumatism. 2009; 60:3241-3250.

(56) References Cited

OTHER PUBLICATIONS

Gossye V, et al. A plant-derived glucocorticoid receptor modulator attenuates inflammation without provoking ligand-induced resistance. Annals of the rheumatic diseases. 2010; 69:291-296.
Goy A, Gilles F. Update on the proteasome inhibitor bortezomib in hematologic malignancies. Clinical lymphoma. 2004; 4:230-237.
Haapakoski R, et al. Intradermal cytosine-phosphate-guanosine treatment reduces lung inflammation but induces IFN-gamma-mediated airway hyperreactivity in a murine model of natural rubber latex allergy. Am J Respir Cell Mol Biol. 2011; 44:639-647.
Herr I, Pfitzenmaier J. Glucocorticoid use in prostate cancer and other solid tumours: implications for effectiveness of cytotoxic treatment and metastases. The Lancet Oncology. 2006; 7:425-430.
Hoesel B, Schmid JA. The complexity of NF-kappaB signaling in inflammation and cancer. Mol Cancer. 2013; 12:86.
Hu X, et al. The antagonists but not partial agonists of glucocorticoid receptor ligands show substantial side effect dissociation. Endocrinology. 2011; 152:3123-3134.
Huynh T, Uaesoontrachoon K, Quinn JL, Tatem KS, Heier CR, Van Der Meulen JH, Yu Q, Harris M, Nolan CJ, Haegeman G, Grounds MD, Nagaraju K. Selective modulation through the glucocorticoid receptor ameliorates muscle pathology in mdx mice. The Journal of pathology. 2013; 231:223-235.
Isikbay M, et al. Glucocorticoid receptor activity contributes to resistance to androgen-targeted therapy in prostate cancer. Hormones & cancer. 2014; 5:72-89.
Jo JC, Kang BW, et al. Initial cytoreductive treatment with thalidomide plus bolus vincristine/doxorubicin and reduced dexamethasone followed by autologous stem cell transplantation for multiple myeloma. Investigational new drugs. 2011; 29:175-181.
Kim SY, et al. Tunicamycin inhibits Toll-like receptor-activated inflammation in RAW264.7 cells by suppression of NF-kappaB and c-Jun activity via a mechanism that is independent of ER-stress and N-glycosylation. European journal of pharmacology. 2013; 721:294-300.
Kleiman A, Tuckermann JP. Glucocorticoid receptor action in beneficial and side effects of steroid therapy: lessons from conditional knockout mice. Molecular and cellular endocrinology. 2007; 275:98-108.
Klopot A, Baida G, Budunova I. Novel glucocorticoid receptor modulator Compound A inhibits skin inflammation and hyperplasia. Journal of Investigative Dermatology. 2009; 131:S27.
Lavery DN, McEwan U. Structure and function of steroid receptor AF1 transactivation domains: induction of active conformations. The Biochemical journal. 2005; 391:449-464.
Lee TW, Proudfoot JR, Thomson DS. A concise asymmetric route for the synthesis of a novel class of glucocorticoid mimetics containing a trifluoromethyl-substituted alcohol. Bioorg Med Chem Lett. 2006; 16:654-657.
Lesovaya E, Yemelyanov A, Kirsanov K, Popa A, Belitsky G, Yakubovskaya M, Gordon LI, Rosen ST, Budunova I. Combination of a selective activator of the glucocorticoid receptor Compound A with a proteasome inhibitor as a novel strategy for chemotherapy of hematologic malignancies. Cell cycle. 2013; 12:133-144.
Liberman AC, et al. Compound A, a dissociated glucocorticoid receptor modulator, inhibits T-bet (Th1) and induces GATA-3 (Th2) activity in immune cells. PloS one. 2012; 7:e35155.
Lin CW, et al. trans-Activation and repression properties of the novel nonsteroid glucocorticoid receptor ligand 2,5-dihydro-9-hydroxy-10-methoxy-2,2,4-trimethyl-5-(1-methylcyclohexen-3-yl)-1H-[1]benzopyrano[3,4-f] quinoline (A276575) and its four stereoisomers. Mol Pharmacol. 2002; 62:297-303.
Louw A, et al. Inhibition of cytochrome P450c11 by biogenic amines and an aziridine precursor, 2-(4-acetoxyphenyl)-2-chloro-N-methyl-ethylammonium chloride. Endocrine research. 2000; 26:729-736.
Louw A, Swart P. *Salsola tuberculatiformis botschantzev* and an aziridine precursor analog mediate the in vivo increase in free corticosterone and decrease in corticosteroid-binding globulin in female Wistar rats. Endocrinology. 1999; 140:2044-2053.
Louw A, et al. Mechanism for the stabilization in vivo of the aziridine precursor—(4-acetoxyphenyl)-2-chloro-N-methyl-ethylammonium chloride by serum proteins. Biochemical pharmacology. 1997; 53:189-197.
Lowenberg M, et al. Novel insights into mechanisms of glucocorticoid action and the development of new glucocorticoid receptor ligands. Steroids. 2008; 73:1025-1029.
Methem A, et al. Administration of glucocorticoids to ovarian cancer patients is associated with expression of the anti-apoptotic genes SGK1 and MKP1/DUSP1 in ovarian tissues. Clinical cancer research: an official journal of the American Association for Cancer Research. 2009; 15:3196-3204.
Miner JN, Hong MH, Negro-Vilar A. New and improved glucocorticoid receptor ligands. Expert opinion on investigational drugs. 2005; 14:1527-1545.
Necela BM, Cidlowski JA. Mechanisms of glucocorticoid receptor action in noninflammatory and inflammatory cells. Proceedings of the American Thoracic Society. 2004; 1:239-246.
Newton R. Molecular mechanisms of glucocorticoid action: what is important? Thorax. 2000; 55:603-613.
Nixon M, Andrew R, Chapman KE. It takes two to tango: dimerisation of glucocorticoid receptor and its anti-inflammatory functions. Steroids. 2013; 78:59-68.
Oh H, Ghosh S. NF-kappaB: roles and regulation in different CD4(+) T-cell subsets. Immunol Rev. 2013; 252:41-51.
Oh S, Hwang ES. The role of protein modifications of T-bet in cytokine production and differentiation of T helper cells. J Immunol Res. 2014; 2014:589672.
Oki Y, et al. Prospective phase II study of rituximab with alternating cycles of hyper-CVAD and high-dose methotrexate with cytarabine for young patients with high-risk diffuse large B-cell lymphoma. British journal of haematology. 2013; 163:611-620.
Pugazhenthi S, et al. Induction of an inflammatory loop by interleukin-1beta and tumor necrosis factor-alpha involves NF-kB and STAT-1 in differentiated human neuroprogenitor cells. PloS one. 2013; 8:e69585.
Ramamoorthy S, Cidlowski JA. Ligand-induced repression of the glucocorticoid receptor gene is mediated by an NCoR1 repression complex formed by long-range chromatin interactions with intragenic glucocorticoid response elements. Molecular and cellular biology. 2013; 33:1711-1722.
Ratman D, et al. How glucocorticoid receptors modulate the activity of other transcription factors: a scope beyond tethering. Molecular and cellular endocrinology. 2013; 380:41-54.
Rauner M, et al. Dissociation of osteogenic and immunological effects by the selective glucocorticoid receptor agonist, compound A, in human bone marrow stromal cells. Endocrinology. 2011; 152:103-112.
Rauner M, et al. Effects of the selective glucocorticoid receptor modulator compound A on bone metabolism and inflammation in male mice with collagen-induced arthritis. Endocrinology. 2013; 154:3719-3728.
Reber LI, et al. A dissociated glucocorticoid receptor modulator reduces airway hyperresponsiveness and inflammation in a mouse model of asthma. Journal of immunology. 2012; 188:3478-3487.
Resche-Rigon M, Gronemeyer H. Therapeutic potential of selective modulators of nuclear receptor action. Current opinion in chemical biology. 1998; 2:501-507.
Reuter KC, et al. Selective glucocorticoid receptor agonists for the treatment of inflammatory bowel disease: studies in mice with acute trinitrobenzene sulfonic acid colitis. The Journal of pharmacology and experimental therapeutics. 2012; 341:68-80.
Richardson PG. Proteasome inhibition in hematologic malignancies. Annals of medicine. 2004; 36:304-314.
Robertson S, et al. Abrogation of glucocorticoid receptor dimerization correlates with dissociated glucocorticoid behavior of compound a. The Journal of biological chemistry. 2010; 285:8061-8075.
Rogatsky I, et al. Distinct glucocorticoid receptor transcriptional regulatory surfaces mediate the cytotoxic and cytostatic effects of glucocorticoids. Molecular and cellular biology. 1999; 19:5036-5049.

(56) References Cited

OTHER PUBLICATIONS

Romano A, et al. Salvage therapy with pegylated liposomal doxorubicin, bortezomib, cyclophosphamide, and dexamethasone in relapsed/refractory myeloma patients. European journal of haematology. 2014; 93:207-213.
Rosen J, Miner JN. The search for safer glucocorticoid receptor ligands. Endocrine reviews. 2005; 26:452-464.
Saksida T, Vujicic M, Nikolic I, Stojanovic I, Haegeman G, Stosic-Grujicic S. Compound A, a selective glucocorticoid receptor agonist, inhibits immunoinflammatory diabetes, induced by multiple low doses of streptozotocin in mice. British journal of pharmacology. 2014; 171:5898-5909.
Schäcke H, et al. Selective glucocorticoid receptor agonists (SEGRAs): novel ligands with an improved therapeutic index. Molecular and cellular endocrinology. 2007; 275:109-117.
Schäcke H, et al. Mechanisms involved in the side effects of glucocorticoids. Pharmacology & therapeutics. 2002; 96:23-43.
Schäcke H, et al. Characterization of ZK 245186, a novel, selective glucocorticoid receptor agonist for the topical treatment of inflammatory skin diseases. British journal of pharmacology. 2009; 158:1088-1103.
Schoepe S, Schacke H, Asadullah K. Test systems for the determination of glucocorticoid receptor ligand induced skin atrophy. Dermatoendocrinol. 2011; 3:175-179.
Shimizu N, Yoshikawa N, Ito N, Maruyama T, Suzuki Y, Takeda S, Nakae J, Tagata Y, Nishitani S, Takehana K, Sano M, Fukuda K, Suematsu M, et al. Crosstalk between glucocorticoid receptor and nutritional sensor mTOR in skeletal muscle. Cell Metab. 2011; 13:170-182.
Stahn C, et al. Molecular mechanisms of glucocorticoid action and selective glucocorticoid receptor agonists. Molecular and cellular endocrinology. 2007; 275:71-78.
Stechschulte LA, Sanchez ER. FKBP51—a selective modulator of glucocorticoid and androgen sensitivity. Current opinion in pharmacology. 2011; 11:332-337.
Striz I, Brabcova E, Kolesar L, Sekerkova A. Cytokine networking of innate immunity cells: a potential target of therapy. Clinical science. 2014; 126:593-612.
Suttitheptumrong A, et al. Compound A, a dissociated glucocorticoid receptor modulator, reduces dengue virus-induced cytokine secretion and dengue virus production. Biochemical and biophysical research communications. 2013; 436:283-288.
Swart P, et al. Biological activities of the shrub Salsola tuberculatiformis botsch.: Contraceptive or Stress Alleviator? BioEssays. 2003; 25:612-619.
Swart P, et al. Micro-assay for sheep 11 beta-hydroxylase activity using high-performance liquid chromatography for steroid analysis. Journal of chromatography. 1988; 442:424-430.
Swart P, et al. Inhibition of cytochrome P-450(11)beta by some naturally occurring acetophenones and plant extracts from the shrub Salsola tuberculatiformis. Planta medica. 1993; 59:139-143.
Tanner TM, et al. Anti-androgenic properties of Compound A, an analog of a non-steroidal plant compound. Molecular and cellular endocrinology. 2003; 201:155-164.
Thiele S, Ziegler N, Tsourdi E, De Bosscher K, Tuckermann JP, Hofbauer LC, Rauner M. Selective glucocorticoid receptor modulation maintains bone mineral density in mice. Journal of bone and mineral research: the official journal of the American Society for Bone and Mineral Research. 2012; 27:2242-2250.
Van der Merwe KJ, et al. Natural products affecting the gestation period of sheep and their mode of action. S Afr J Sci 72. 1976; 72:184.
Van Loo G, Sze M, Bougarne N, Praet J, McGuire C, Ullrich A, Haegeman G, Prinz M, Beyaert R, De Bosscher K. Anti-inflammatory properties of a plant-derived nonsteroidal, dissociated glucocorticoid receptor modulator in experimental autoimmune encephalomyelitis. Molecular endocrinology. 2010; 24:310-322.
Van Rossum EF, et al. Glucocorticoid resistance. Endocrine development. 2011; 20:127-136.

Vandevyver S, Dejager L, Libert C. On the trail of the glucocorticoid receptor: into the nucleus and back. Traffic. 2012; 13:364-374.
Vandevyver S, Dejager L, Tuckermann J, Libert C. New insights into the anti-inflammatory mechanisms of glucocorticoids: an emerging role for glucocorticoid-receptor-mediated transactivation. Endocrinology. 2013; 154:993-1007.
Vayssiere BM, Dupont S, Choquart A, Petit F, Garcia T, Marchandeau C, Gronemeyer H, Resche-Rigon M. Synthetic glucocorticoids that dissociate transactivation and AP-1 transrepression exhibit antiinflammatory activity in vivo. Molecular endocrinology. 1997; 11:1245-1255.
Volden PA, Conzen SD. The influence of glucocorticoid signaling on tumor progression. Brain Behav Immun. 2013; 30:S26-31.
Wallace AD, et al. Lysine 419 targets human glucocorticoid receptor for proteasomal degradation. Steroids. 2010; 75:1016-1023.
Wallace AD, Cidlowski JA. Proteasome-mediated glucocorticoid receptor degradation restricts transcriptional signaling by glucocorticoids. The Journal of biological chemistry. 2001; 276:42714-42721.
Wan YY. GATA3: a master of many trades in immune regulation. Trends Immunol. 2014; 35:233-242.
Wheeler OH. The Girard reagents. Chem Reviews. 1962; 62:205-221.
Whitehouse MW. Anti-inflammatory glucocorticoid drugs: reflections after 60 years. Inflammopharmacology. 2011; 19:1-19.
Wiederrecht G, et al. Characterization of high molecular weight FK-506 binding activities reveals a novel FK-506-binding protein as well as a protein complex. The Journal of biological chemistry. 1992: 267:21753-21760.
Wu W, et al. Microarray analysis reveals glucocorticoid-regulated survival genes that are associated with inhibition of apoptosis in breast epithelial cells. Cancer research. 2004; 64:1757-1764.
Wust S, et al. Therapeutic and adverse effects of a non-steroidal glucocorticoid receptor ligand in a mouse model of multiple sclerosis. PloS one. 2009; 4:e8202.
Yano A, et al. Glucocorticoids suppress tumor lymphangiogenesis of prostate cancer cells. Clinical cancer research: an official journal of the American Association for Cancer Research. 2006; 12:6012-6017.
Yemelyanov A, Bhalla P, Yang X, Ugolkov A, Iwadate K, Karseladze A, Budunova I. Differential targeting of androgen and glucocorticoid receptors induces ER stress and apoptosis in prostate cancer cells: a novel therapeutic modality. Cell cycle. 2012; 11:395-406.
Yemelyanov A, Czwornog J, Chebotaev D, Karseladze A, Kulevitch E, Yang X, Budunova I. Tumor suppressor activity of glucocorticoid receptor in the prostate. Oncogene. 2007; 26:1885-1896.
Yemelyanov A, Czwornog J, Gera L, Joshi S, Chatterton RT Jr., Budunova I. Novel steroid receptor phyto-modulator compound a inhibits growth and survival of prostate cancer cells. Cancer research. 2008; 68:4763-4773.
Yudt MR, Cidlowski JA. The glucocorticoid receptor: coding a diversity of proteins and responses through a single gene. Molecular endocrinology. 2002; 16:1719-1726.
Zhang L, Insel PA. Bcl-2 protects lymphoma cells from apoptosis but not growth arrest promoted by cAMP and dexamethasone. American journal of physiology Cell physiology. 2001; 281:C1642-1647.
Zhang Y, Gu W, He L, Sun B. Th1/Th2 cell's function in immune system. Adv Exp Med Biol. 2014; 841:45-65.
Zhang Y, Gu W, Sun B. TH1/TH2 cell differentiation and molecular signals. Adv Exp Med Biol. 2014; 841:15-44.
Zhang Z, Zhang ZY, Schluesener HJ. Compound A, a plant origin ligand of glucocorticoid receptors, increases regulatory T cells and M2 macrophages to attenuate experimental autoimmune neuritis with reduced side effects. Journal of immunology. 2009; 183:3081-3091.
Swart et al., Inhibition of cytochrome P-450(11)beta by some naturally occurring acetophenones and plant extracts from the shrub Salsola tuberculatiformis. Planta medica. 1993; 59:139-143.
Swart et al., Biological activities of the shrub Salsola tuberculatiformis botsch.: Contraceptive or Stress Alleviator? BioEssays. 2003; 25:612-619.

(56) References Cited

OTHER PUBLICATIONS

Herr et al., Glucocorticoid use in prostate cancer and other solid tumours: implications for effectiveness of cytotoxic treatment and metastases. The Lancet Oncology. 2006; 7:425-430.
Zhang et al., Bcl-2 protects lymphoma cells from apoptosis but not growth arrest promoted by cAMP and dexamethasone. American Journal of Physiology Cell Physiology. 2001; 281:C1642-1647.
Melhem et al., Administration of glucocorticoids to ovarian cancer patients is associated with expression of the anti-apoptotic genes SGK1 and MKP1/DUSP1 in ovarian tissues. Clinical Cancer Research: an official journal of the American Association for Cancer Research. 2009; 15:3196-3204.
Isikbay et al., "Glucocorticoid receptor activity contributes to resistance to androgen-targeted therapy in prostate cancer." Hormones & Cancer. 2014; 5:72-89.
Volden et al., The influence of glucocorticoid signaling on tumor progression. Brain Behav Immun. 2013; 30:S26-31.
Yemelyanov et al., "Differential targeting of androgen and glucocorticoid receptors induces ER stress and apoptosis in prostate cancer cells: a novel therapeutic modality." Cell Cycle. 2012; 11:395-406.
Wu et al., "Microarray analysis reveals glucocorticoid-regulated survival genes that are associated with inhibition of apoptosis in breast epithelial cells." Cancer Research. 2004; 64:1757-1764.
Van Rossum et al., "Glucocorticoid resistance." Endocrine Development. 2011; 20: 127-136.
Ramamoorthy et al., "Ligand-induced repression of the glucocorticoid receptor gene is mediated by an NCoR1 repression complex formed by long-range chromatin interactions with intragenic glucocorticoid response elements." Molecular and Cellular Biology. 2013; 22:1711-1722.
Wallace et al., Proteasome-mediated glucocorticoid receptor degradation restricts transcriptional signaling by the glucocorticoids. The Journal of Biological Chemistry. 2001; 276:42714-42721.
Gossye et al., "A plant-derived glucocorticoid receptor modulator attenuates inflammation without provoking ligand-induced resistance." Annals of the Rheumatic Diseases. 2010; 69:291-296.
Lesovaya et al., Combination of a selective activator of the glucocorticoid receptor Compound A with a proteasome inhibitor as a novel strategy for chemotherapy of hematologic malignancies. Cell Cycle. 2013; 12:133-144.
Dewint et al., "A plant-derived ligand favoring monomeric glucocorticoid receptor conformation with impaired transactivation potential attenuates collagen-induced arthritis." Journal of Immunology. 2008; 180:2608-2615.
Wiederrecht et al., "Characterization of high molecular weight FK-506 binding activities reveals a novel FK-506-binding protein as well as a protein complex." The Journal of Biological Chemistry. 1992; 267:21753-21760.
Stechschulte et al., FKBP51—a selective modulator of glucocorticoid and androgen sensitivity. Current Opinion in Pharmacology. 2011; 11:332-337.
Chun et al., "Dexamethasone-induced FKBP51 expression in peripheral blood mononuclear cells could play a role in predicting the response of asthmatics to treatment with corticosteroids." Journal of Clinical Immunology. 2011; 31:122-127.
Barnes, "Anti-inflammatory actions of glucocorticoids: molecular mechanisms." Clinical Science. 1998; 94:557-572.

Resche-Rigon et al., "Therapeutic potential of selective modulators of nuclear receptor action." Current Opinion in Chemical Biology. 1998; 2:501-507.
Vayssiere et al., "Synthetic glucocorticoids that dissociate transactivation and AP-1 transrepression exhibit antiinflammatory activity in vivo." Molecular Endocrinology. 1997; 11:1245-1255.
Kleiman et al., "Glucocorticoid receptor action in beneficial and side effects of steroid therapy: lessons from conditional knockout mice." Molecular and Cellular Endocrinology. 2007; 275:98-108.
De Bosscher et al., "Classic glucocorticoids versus non-steroidal glucocorticoid receptor modulators: survival of the fittest regulator of the immune system?" Brain Behav Immun. 2010; 24:1035-1042.
Wust et al., "Therapeutic and adverse effects of a non-steroidal glucocorticoid receptor ligand in a mouse model of multiple sclerosis." PloS One. 2009; 4:e8202.
Hyunh et al., "Selective modulation through the glucocorticoid receptor ameliorates muscle pathology in mdx mice." The Journal of Pathology. 2013; 231:223-235.
Saksida et al., "Compound A, a selective glucocorticoid receptor agonist, inhibits immunoinflammatory diabetes, induced by multiple low doses of streptozotocin in mice." British Journal of Pharmacology. 2014; 171:5898-5909.
Thiele et al., "Selective glucocorticoid receptor modulation maintains bone mineral density in mice." Journal of Bone and Mineral Research: the official journal of the American Society for Bone and Mineral Research. 2012; 27:2242-2250.
Rauner et al., "Dissociation of osteogenic and immunological effects by the selective glucocorticoid receptor agonist, compound A, in human bone marrow stromal cells." Endocrinology. 2011; 152:103-112.
Schacke et al., "Mechanisms involved in the side effects of glucocorticoids. Pharmacology & therapeutics." 2002; 96:23-43.
Klopot et al., "Novel glucocorticoid receptor modulator Compound A inhibits skin inflammation and hyperplasia." Journal of Investigative Dermatology. 2009; 131:S27.
Schoepe et al., "Test systems for the determination of glucocorticoid receptor ligand induced skin atrophy." Dermatoendocrinol. 2011; 3:175-179.
Baida et al., "REDD1 functions at the crossroads between the therapeutic and adverse effects of topical glucocorticoids." EMBO Mol Med. 2015; 7:42-58.
Shimuzu et al., "Crosstalk between glucocorticoid receptor and nutritional sensor mTOR in skeletal muscle." Cell Metab. 2011; 13:170-182.
Van Loo et al., "Anti-inflammatory properties of a plant-derived nonsteroidal, dissociated glucocorticoid receptor modulator in experimental autoimmune encephalomyelitis. Molecular endocrinology." 2010; 24:310-322.
Yemelyanov et al., Novel steroid receptor phyto-modulator compound a inhibits growth and survival of prostate cancer cells. Cancer Res. Jun. 15, 2008;68(12):4763-73. doi: 10.1158/0008-5472.CAN-07-6104.
Araora et al., Glucocorticoid receptor confers resistance to antiandrogens by bypassing androgen receptor blockade. Cell. Dec. 5, 2013;155(6):1309-22. doi.
Lesovaya et al., Discovery of Compound A—a selective activator of the glucocorticoid receptor with anti-inflammatory and anti-cancer activity. Oncotarget. Oct. 13, 2015;6(31):30730-44. doi: 10.18632/oncotarget.5078. Review.

\* cited by examiner

A. Docking into GR LBD

B. Docking into AR LBD

C. H-bond formation

GR-DEX:
Asn 564
Arg 611
Gln 642
Thr 739

GR-CpdA:
Asn 564
Arg 611
Gln 570

AR-DHT:
Arg 752
Asn 705
Thr 877

AR-CpdA:
Arg 752
Asn 705

A.

B.

C.

A.

B.

A. Spontaneous apoptosis by CpdA
(Western blotting)

B. Sensitization to TNF-induced apoptosis by CpdA
(Western blotting)

SUBSTITUTED PHENYL AZIRIDINE PRECURSOR ANALOGS FOR INHIBITING ANDROGEN-INDEPENDENT PROSTATE CANCER CELL GROWTH

CROSS-REFERENCE TO RELATED APPLICATIONS

The present application is a continuation of U.S. application Ser. No. 15/487,036, filed on Apr. 13, 2017, which application was published on Aug. 3, 2017, as U.S. Publication No. 2017/0216249, which application is a continuation of U.S. application Ser. No. 14/963,788, filed on Dec. 9, 2015, which application was published on Mar. 31, 2016, as U.S. Publication No. 2016/0089354, which application is a continuation of U.S. application Ser. No. 14/057,518, filed on Oct. 18, 2013, which application was published on Feb. 13, 2014, as U.S. Publication No. 2014/0045938, and which application is a continuation of U.S. application Ser. No. 12/335,911, filed on Dec. 16, 2008, which application was published on Jun. 18, 2009, as U.S. Publication No. 20090156672, which application claims the benefit under 35 U.S.C. § 119(e) to U.S. Provisional Application No. 61/014,225, filed on Dec. 17, 2007, the contents of which are incorporated herein by reference in their entireties.

BACKGROUND

Steroid hormone receptors such as androgen receptor (AR) or glucocorticoid receptor (GR) are observed transcription factors that regulate gene expression. In non-activated cells each receptor resides in the cytoplasm in a complex with chaperone proteins. Upon activation by corresponding steroid hormones (e.g., where GR is activated by glucocorticoids and AR is activated by androgens) steroid hormone receptors dissociate from the chaperones, form homo-dimers and enter the nucleus where they interact with the regulatory sequences in gene promoters.

Signaling mediated through the steroid hormone receptors plays a pivotal role in the development of diseases and disorders such as prostate cancer (PC). Androgens and androgen receptor (AR) promote the development and progression of PC (Feldman et al., and Heinlein et al.). In contrast, signaling mediated by the glucocorticoid receptor (GR) plays a tumor suppressor role in prostate (Dondi et al., Nishimura et al., Smith et al., Yano et al., and Yemelyanov et al.). As activation of AR and GR have opposite effect on PC cells, the multi-target steroid receptor modulators that positively regulate GR- and negatively regulate AR-mediated signaling may be more effective for PC chemotherapy than single-target compounds.

2-(4-acetoxyphenyl)-2-chloro-N-methyl-ethylammonium chloride, also called Compound A (CpdA), is a synthetic analog of the highly labile aziridine precursor found in the African shrub *Salsola tuberculatiformis* Botschantzev (Swart et al. 2003). The aqueous extract of this plant has been used by Bushmen women as a traditional medicine (Swart et al. 2003). It has been shown recently that CpdA directly interacts with steroid receptors AR and GR (De Bosscher et al. 2005, and Tanner et al.). Importantly, CpdA inhibits AR function and strongly enhances the anti-inflammatory function of GR. CpdA does not compete with androgen for AR binding, but similar to well-characterized anti-androgens, represses the activation of AR by inhibition of the androgen-dependent interaction between $NH_2$- and COOH-terminal domains of the AR (Tanner et al.), At the same time, CpdA acts as a non-steroidal GR ligand as it competes with glucocorticoids for GR binding and induces GR translocation into the nucleus (De Bosscher et al, 2005). There are two major mechanisms underlying gene regulation by GR: (i) positive regulation (transactivation) that requires GR binding to glucocorticoid-response elements in gene promoters; and (ii) negative regulation (transrepression) that is mediated via negative interaction between GR and other transcription factors, such as NF-κB and AP-1 (De Bosscher et al. 2003, Schacke et al. 2002, and Yemelyanov et al.). It is well understood that many therapeutic anti-inflammatory effects of glucocorticoids are mediated via gene transrepression. In contrast, many undesirable side effects are mediated via DNA-dependent transactivation. It was shown that CpdA possesses the properties of the "dissociated" GR ligand that does not affect GR transactivation potential but induces GR-mediated transrepression (De Bosscher et al. 2005, and Tanner et al.). Furthermore, in in vivo experiments, CpdA acts as a strong anti-inflammatory compound with reduced side effects (De Bosscher et al. 2005).

The effect of CpdA on cell growth has never been studied. Here, the effect of CpdA on the growth of several PC cell lines and non-transformed prostate cells is studied. CpdA is observed not to significantly affect non-transformed prostate cells, but to have strong growth inhibitory and pro-apoptotic effects in several prostate carcinoma cell lines. CpdA is observed to induce the overall "normalization" of PC cell phenotype. Moreover, CpdA is much more effective in terms of inhibition of growth and survival of PC cells than glucocorticoids. This suggests that CpdA is a unique multi-target steroid receptor modulator that could be used in the future for the treatment of patients with PC and other diseases or disorders that are mediated by steroid hormone receptors.

SUMMARY

Disclosed are methods, compounds, and pharmaceutical compositions for treating diseases, disorders or conditions in a patient in need thereof. The diseases, disorders, or conditions typically are associated with steroid receptor activities and are responsive to modulation of steroid receptor activities.

The methods typically include administering to the patient a therapeutically effective amount of a compound having formula (I), its aziridine derivatives, analogs, or pharmaceutically acceptable salts thereof:

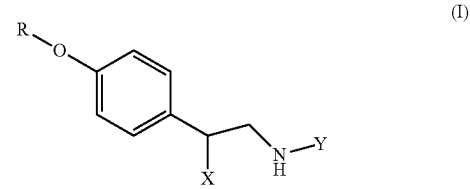

(I)

where R is a hydrogen or —C(O)—Z, where Z is a branched or straight chain. $C_1$-$C_6$ alkyl group;
X is a hydrogen, hydroxyl, halogen or a leaving group; and
Y is a hydrogen or a branched or straight chain $C_1$-$C_6$ alkyl group. Optionally R may be acetyl (i.e., —C(O)—$CH_3$); optionally, X may be halogen (e.g., chloride, bromide, or fluoride); and optionally, Y may be methyl, ethyl, propyl, or butyl (desirably methyl). Compounds having formula (I), its aziridine derivatives, analogs, or pharmaceutically acceptable salts thereof may include compounds having formula (II), (III), (IV), or (V):

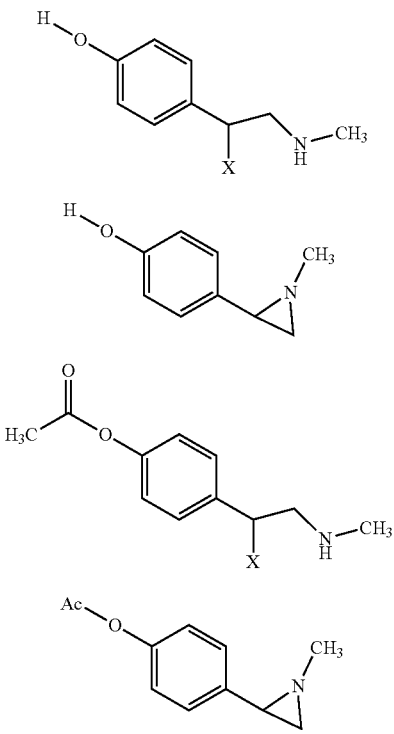

A compound having formula (I), or aziridine derivatives, analogs, or pharmaceutically acceptable salts thereof may include 2-(4-acetoxyphenyl)-2-chloro-N-methylethyl-ammonium chloride, otherwise known as CpdA, which is a stable analog of an aziridine precursor from the African shrub *Salsola tuberculatiformis* Botschantzev. CpdA has the formula:

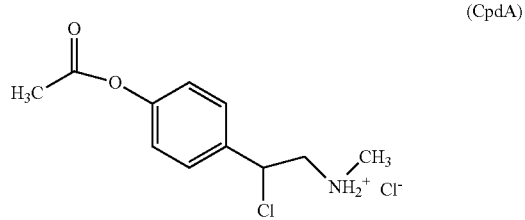

(CpdA)

The compounds disclosed herein (e.g., CpdA) may inhibit the growth of target cells or kill target cells. For example, the compound may inhibit the growth of cancer cells or kill cancer cells such as prostate cancer cells (e.g., LNCaP, DU145, and PC3 cells), In further embodiments, the compound does not significantly inhibit the growth of non-cancerous cells or kill other non-cancerous cells (e.g., non-transformed prostate cells, hepatocytes, cardiomyocytes, and skeletal muscle cells).

The compounds disclosed herein (e.g., CpdA) may sensitize cells to apoptosis, whereby cells exposed to the compound are more likely to undergo apoptosis after being exposed to apoptotic stimuli relative to cells that are not exposed to the compound. For example, the compound may sensitize cancer cells, such as prostate cancer cells to apoptosis (e.g., apoptosis effected by apoptotic stimuli such as chemotherapy). In further embodiments, the compound does not significantly sensitize non-cancerous cells (e.g., non-transformed prostate cells, hepatocytes, cardiomyocytes, and skeletal muscle cells) to apoptosis.

The compounds disclosed herein (e.g., CpdA) may bind to steroid receptors such as glucocorticoid receptor (GR), androgen receptor (AR), or both receptors. In some embodiments, the compound is a ligand for GR and induces GR transrepression activity in cells (e.g., cancer cells such as LNCaP, DU145, and PC3 cells). In some embodiments the compound inhibits AR transcriptional activity in cells (e.g., cancer cells such as LNCaP, DU145, and PC3 cells). In some embodiments, the compound may bind to steroidogenic enzymes (e.g., cytochrome P450c1), plasma steroid-binding globulins (e.g. corticosteroid binding globulin), or both.

The disclosed methods may include treating prostate cancer or prostate hyperplasia in a patient in need thereof (e.g., androgen-independent or androgen-dependent prostate cancer or hyperplasia). In some embodiments, the methods may include inhibiting prostate cancer cell growth in a patient having androgen-independent prostate cancer, the method comprising administering to the patient a therapeutically effective amount of a compound having formula (I), or aziridine derivatives, analogs, or pharmaceutically acceptable salts thereof, as disclosed herein. In further embodiments, the methods may include treating androgen-dependent prostate hyperplasia (e.g., androgen-dependent benign prostatic hyperplasia (BPH)).

The disclosed methods may include sensitizing prostate cancer cells to apoptosis in a patient in need thereof, the method comprising: step (a), administering an effective amount of a compound having formula (I), or aziridine derivatives, analogs, or pharmaceutically acceptable salts thereof, as disclosed herein; and step (b), administering an effective amount of a pro-apoptotic stimuli (e.g., chemotherapy and radiation therapy). Preferably, step (a) is performed before step (b) or concurrently with step (b).

The disclosed methods may include treating prostate cancer in a patient in need thereof, the methods comprising: step (a), assessing expression of a marker selected from the group consisting of hespin, α-methylacyl-CoA racemase, and maspin; and step (b), based on the assessed expression, administering an effective amount of a compound having formula (I), or aziridine derivatives, analogs, or pharmaceutically acceptable salts thereof, as disclosed herein. Preferably, step (a) is performed before step (b) or concurrently with step (b).

The disclosed methods may include treating prostate cancer in a patient in need thereof and assessing the therapeutic effect of the treatment. The methods may comprise: step (a), administering an effective amount of a compound having formula (I), or aziridine derivatives, analogs, or pharmaceutically acceptable salts thereof, as disclosed herein; and step (b), assessing expression of a marker selected from the group consisting of hespin, α-methylacyl-CoA racemase, and maspin, thereby assessing the therapeutic effect of the compound having formula (I). The method further may include: step (c), administering (or not administering) an effective amount of a compound for treating prostate cancer (e.g., a compound having formula (I), or aziridine derivatives, analogs, or pharmaceutically acceptable salts thereof, as disclosed herein, or another compound for treating prostate cancer) based on the assessment in step (b).

The disclosed methods may include treating acne vulgaris in a patient in need thereof, the method comprising administering to the patient a therapeutically effective amount of a compound having formula (I), or aziridine derivatives, analogs, or pharmaceutically acceptable salts thereof, as disclosed herein. The compound may be formulated for delivery by a suitable route (e.g., oral, intravenous, intramuscular, subcutaneous, pulmonary, and topical).

The disclosed methods may include treating alopecia in a patient in need thereof (e.g., androgen-dependent alopecia), the method comprising administering to the patient a therapeutically effective amount of a compound having formula (I), or aziridine derivatives, analogs, or pharmaceutically acceptable salts thereof, as disclosed herein. The compound may be formulated for delivery by a suitable route (e.g., oral, intravenous, intramuscular, subcutaneous, pulmonary, and topical).

Also disclosed are pharmaceutical compositions comprising: (a) a therapeutically effective amount of a compound having formula (I), or aziridine derivatives, analogs, or pharmaceutically acceptable salts thereof; and (b) a pharmaceutical carrier, diluent, or excipient. The pharmaceutical composition may be formulated for delivery by any suitable route (e.g., oral, intravenous, intramuscular, subcutaneous, pulmonary, and topical).

DETAILED DESCRIPTION

Figure 1:
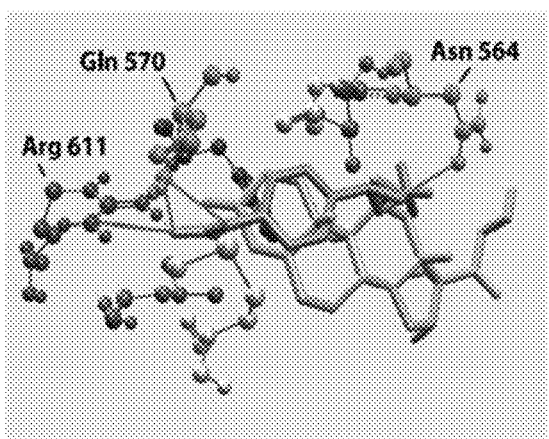
FIG. 1. Virtual Docking: Analysis of CpdA binding at GR and AR LBD. A. & B. Virtual docking was performed by Molegro software package dedicated to drug design and modeling of protein interactions using PDB files of GR and AR ligand binding domains (LBD) from the "PDB" organization website, including PDB files of CpdA, DEX, and DHT. C. CpdA, DHT, and DEX were observed to form hydrogen bonds with the highlighted amino acids when bound to GR and AR LBDs.
Figure 1:
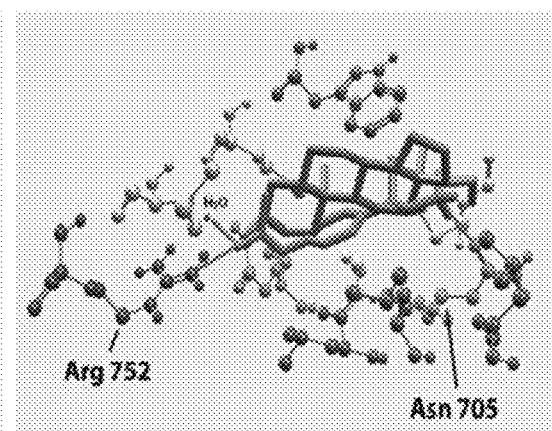

The present invention is described herein using several definitions, as set forth below and throughout the application.

Unless otherwise specified or indicated by context, the terms "a", "an", and "the" mean "one or more." For example, "a compound" should be interpreted to mean "one or more compounds."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus≤10% of the particular term and "substantially" and "significantly" will mean plus or minus>10% of the particular term.

As used herein, the terms "include" and "including" have the same meaning as the terms "comprise" and "comprising." For example, a "pharmaceutical composition that includes a compound" should be interpreted to mean "a pharmaceutical composition that comprises a compound."

The compounds disclosed herein may modulate steroid receptor activities. As used herein, "steroid receptor activities" include glucocorticoid receptor activity, androgen receptor activity, and other steroid receptor activities. Receptor activity may include one or more of ligand binding, transcriptional activation of target genes, and repression of expression for target genes.

As used herein, the phrase "therapeutically effective amount" shall mean that drug dosage that provides the specific pharmacological response for which the drug is administered in a significant number of subjects in need of such treatment. A therapeutically effective amount of a drug that is administered to a particular subject in a particular instance will not always be effective in treating the conditions/diseases described herein, even though such dosage is deemed to be a therapeutically effective amount by those of skill in the art.

As used herein, a "patient" may be interchangeable with "subject" and means an animal, which may be a human or non-human animal, in need of treatment. Non-human animals may include dogs, cats, horses, cows, pigs, sheep, and the like.

A "patient in need thereof" may include a patient having a disease, disorder, or condition that is responsive to modulation of one or more steroid receptor activities. Modulation may include induction or inhibition. For example, a "patient in need thereof" may include a patient having a disease, disorder, or condition that is responsive to a treatment method that includes induction of glucocorticoid receptor transrepression activity, inhibition of androgen receptor transcriptional activity, or both.

A "patient in need thereof" may include a patient having cancer or at risk for developing cancer. A patient having cancer may include a patient having prostate cancer or prostate hyperplasia (e.g., benign prostatic hyperplasia or "BPH"), which may include androgen-independent prostate cancer, androgen-dependent prostate cancer, androgen-independent hyperplasia, and androgen-dependent hyperplasia. A patient having androgen-independent prostate cancer may include a patient that has undergone anti-androgen therapy and now has prostate cancer that exhibits resistance to the anti-androgen therapy.

A "patient in need thereof" may include a patient that will benefit from apoptotic sensitization prior to being subjected to "pro-apoptotic stimuli" (e.g., as part of a cancer therapy). As used herein, "pro-apoptotic stimuli" may include any physical, chemical, or biological agent administered at a suitable dosage for inducing apoptosis in a targeted cell. "Pro-apoptotic stimuli" may include radiation and chemotherapy. "Pro-apoptotic stimuli" may include or target one or more genes or gene products including but not limited to TNF-α, NF-κB, TRAIL, Apoptin, Caspases, Bax, Bcl-2, Bcl-XL, p53, Retinoblastoma, FHIT, PI3κ, Ras, BCR-ABL, Proteasome inhibitors, c-raf, c-myb, and Cell cycle modulators. "Pro-apoptotic stimuli" may utilize or include administering recombinant proteins, gene therapy, oligonucleotides (e.g., anti-sense oligodeoxynucleotides), lonidamine, arsenite, PK 11195, LY294002, STI-571, PS-341, UCN-01, and flavopiridol.

A "patient in need thereof" may include a patient having a disease, condition, or disorder that will benefit from inhibiting the activity of one or more oncogenic transcription factors or one or more upstream regulatory kinases for the oncogenic transcription factors. For example, a "patient in need thereof" may include a patient having a disease, condition, or disorder that will benefit from inhibiting the activity of one or more of the oncogenic transcription factors NF-κB, AP-1, and Elk-1/Ets-1; from inhibiting one or more upstream regulatory kinases for NF-κB, AP-1, Elk-1/Ets-1 (e.g., Akt and Mek-½); or from inhibiting both the one or more oncogenic transcription factors and the one or more upstream regulatory kinases.

A "patient in need thereof" may include a patient having alopecia or baldness or at risk for developing alopecia or baldness. "Baldness" may include full or partial baldness in a male or female patient relative to a patient population having similar demographics as the male or female patient. "Baldness" may include male pattern baldness. A patient in need thereof may include a patient having androgenic or androgen-dependent alopecia.

A "patient in need thereof" may include a patient having acne vulgaris or at risk for developing acne vulgaris. A patient having acne vulgaris or at risk for developing acne vulgaris may include a patient having androgen-dependent or androgen-independent acne vulgaris or at risk for developing androgen-dependent or androgen-independent acne vulgaris.

As disclosed herein, compounds having formula (I), or aziridine derivatives, analogs, or pharmaceutically acceptable salts thereof may be administered to patients in need thereof in treatment methods or prevention methods. For example, the compounds may be administered as a pharmaceutical composition. The compounds having formula (I), or aziridine derivatives, analogs, or pharmaceutically acceptable salts thereof may include compounds having formula (II), (III), (IV), or (V). Compounds having formula (I), or aziridine derivatives, analogs, or pharmaceutically acceptable salts thereof may include 2-(4-acetoxyphenyl)-2-chloro-N-methylethyl-ammonium chloride, otherwise known as CpdA, which is a stable analog of an aziridine precursor from the African shrub *Salsola tuberculatiformis* Boschantzev. Investigation of the active compound in *Salsola tuberculatiformis* Botschantzev lead to the isolationg of an active, but labile, fraction isolated by HPLC and called S2. (See Swart et al. 1993) Analysis of the S2 fraction suggested the presence of a highly reactive hydroxyphenyl aziridine or its precursor. (See van der Merwe et al.) This highly reactive hydroxyphenyl aziridine and a generic precursor are represented by formula (III) and formula (II), respectively, as disclosed herein. The labile nature of the active compound in the S2 fraction lead to the synthesis of a more stable analog, compound A (2-(4-acetoxyphenyl)-2-chloro-N-methylethyl-ammonium chloride), which cyclizes to the corresponding aziridine under physiological conditions. (Sec Louw et al. 1997.) The cyclized aziridine of CpdA is represented by formula (V), as disclosed herein.

Contemplated herein are compounds and pharmaceutical compositions comprising compounds having formula (I), or aziridine derivatives, analogs, or pharmaceutically acceptable salts thereof. In some embodiments, compounds contemplated herein include compounds having formula (II), (III), (IV), (V), or CpdA. Referring to the PubChem Database provided by the National Center for Biotechnology Information (NCBI) of the National Institute of Health (NIH) at its website, compounds contemplated herein may include the compound referenced by compound identification (CID) No. 9838147 "Glucocorticoid Receptor Modulator, CpdA: 2-(4-Acetoxyphenyl)-2-chloro-N-methyl)ethylammonium chloride), which entry is incorporated herein by reference in its entirety. Compounds contemplated herein having formula (I), or aziridine derivatives, analogs, or pharmaceutically acceptable salts thereof also include compounds referenced by compound identification (CID) Nos.: 127006, 9838148, 17981414, 18451555, 19880701, 19880702, 19880708, and 19880709, which entries are incorporated herein by reference in their entireties.

In some embodiments, the compounds may be formulated as pharmaceutical compositions that include: (a) a therapeutically effective amount of a compound as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action (e.g., at the prostate) is about 2 to 10 µM.

The compound may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compound may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compound may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compound may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The pharmaceutically effective compounds of formula (I), or aziridine derivatives thereof, and pharmaceutically acceptable salts thereof (i.e., as an "active ingredient") may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compound may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Illustrative Embodiments

The following embodiments are illustrative and are not intended to limit the scope of the claimed subject matter.

Embodiment 1

A method of inhibiting prostate cancer cell growth in a patient having androgen-independent prostate cancer, the method comprising administering to the patient a therapeutically effective amount of a compound having formula (I), or aziridine derivatives, analogs, or pharmaceutically acceptable salts thereof

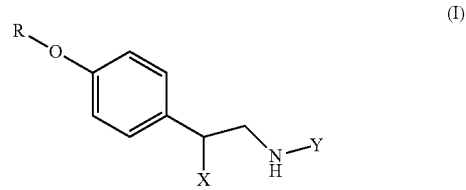

where R is a hydrogen or —C(O)—Z, where Z is a branched or straight chain $C_1$-$C_6$ alkyl group;

X is a hydrogen, hydroxyl, halogen or leaving group; and

Y is a hydrogen or a branched or straight chain $C_1$-$C_6$ alkyl group.

Embodiment 2

The method of embodiment 1, where R is acetyl (i.e., —C(O)—CH$_3$).

Embodiment 3

The method of embodiment 1 or 2, where X is a halogen.

Embodiment 4

The method of embodiment 3, where the halogen is chloride, bromide, or fluoride.

Embodiment 5

The method of any of embodiments 1-4, where Y is methyl, ethyl, propyl, or butyl.

Embodiment 6

The method of embodiment 5, where Y is methyl.

Embodiment 7

The method of any of embodiments 1-6, where the compound having formula (I), or aziridine derivatives, analogs, or pharmaceutically acceptable salts thereof is CpdA.

Embodiment 8

The method of any of embodiments 1-7, where the compound sensitizes prostate cancer cells to the apoptotic effect of TNF-α.

Embodiment 9

The method of any of embodiments 1-7, where the compound sensitizes DU145 cells to the apoptotic effect of TNF-α.

Embodiment 10

The method of any of embodiments 1-9, where the compound binds to glucocorticoid receptor.

Embodiment 11

The method of any of embodiments 1-10, where the compound inhibits androgen receptor transcriptional activity in prostate cancer cells.

Embodiment 12

The method of any of embodiments 1-10, where the compound inhibits androgen receptor transcriptional activity in LNCaP cells.

Embodiment 13

A method of sensitizing prostate cancer cells to apoptosis comprising administering: (a) an effective amount of a compound having formula (I), or aziridine derivatives, analogs, or pharmaceutically acceptable salts thereof, where R is a hydrogen or —C(O)—Z, and Z is a branched or straight chain C$_1$-C$_6$ alkyl group; X is a hydrogen, hydroxyl, or halogen; and Y is a branched or straight chain C$_1$-C$_6$ alkyl group; and (b) an effective amount of a pro-apoptotic stimuli.

Embodiment 14

The method of embodiment 13, where the pro-apoptotic stimuli comprises chemotherapy.

Embodiment 15

The method of claim 13, where R is acetyl (i.e. —C(O)—CH$_3$).

Embodiment 16

The method of embodiment 14 or 15, where X is a halogen.

Embodiment 17

The method of embodiment 16, where the halogen is chloride, bromide, or fluoride.

Embodiment 18

The method of any of embodiments 13-17, where Y is methyl, ethyl, propyl, or butyl.

Embodiment 19

The method of embodiment 18, where Y is methyl.

Embodiment 20

The method of any of embodiments 13-19, where the compound having formula (I), or aziridine derivatives, analogs, or pharmaceutically acceptable salts thereof is CpdA.

Embodiment 21

The method of any of embodiments 13-20, where the compound sensitizes prostate cancer cells to the apoptotic effect of TNF-α.

Embodiment 22

The method of any of embodiments 13-20, where the compound sensitizes DU145 to the apoptotic effect of TNF-α.

Embodiment 23

The method of any of embodiments 13-22, where the compound binds to glucocorticoid receptor.

Embodiment 24

The method of any of embodiments 13-23, where the compound inhibits androgen receptor transcriptional activity in prostate cancer cells.

Embodiment 25

The method of any of embodiments 13-23, where the compound inhibits androgen receptor transcriptional activity in LNCaP cells.

Embodiment 26

A method of treating prostate cancer in a patient in need thereof comprising: (a) assessing expression of a marker selected from the group consisting of hespin, α-methylacyl-CoA racemase, and maspin; and (b) based on the assessed expression administering an effective amount of a compound having formula (I), or aziridine derivatives, analogs, or pharmaceutically acceptable salts thereof, where R is a hydrogen or —C(O)—Z, and Z is a branched or straight chain $C_1$-$C_6$ alkyl group; X is a hydrogen, hydroxyl, or halogen; and Y is a branched or straight chain $C_1$-$C_6$ alkyl group.

Embodiment 27

A method of treating prostate cancer in a patient in need thereof comprising: (a) administering an effective amount of a compound having formula (I), or aziridine derivatives, analogs, or pharmaceutically acceptable salts thereof, where R is a hydrogen or —C(O)—Z, and Z is a branched or straight chain $C_1$-$C_6$ alkyl group; X is a hydrogen, hydroxyl, or halogen; and Y is a branched or straight chain $C_1$-$C_6$ alkyl group; and (b) assessing expression of a marker selected from the group consisting of hespin, α-methylacyl-CoA racemase, and maspin, thereby assessing the therapeutic effect of the compound.

Embodiment 28

A method of benign prostate hyperplasia in a patient in need thereof, the method comprising administering to the patient a therapeutically effective amount of a compound having formula (I), or aziridine derivatives, analogs, or pharmaceutically acceptable salts thereof: where R is a hydrogen or —C(O)—Z, and Z is a branched or straight chain $C_1$-$C_6$ alkyl group; X is a hydrogen, hydroxyl, or halogen; and Y is a branched or straight chain $C_1$-$C_6$ alkyl group.

Embodiment 29

A method of treating acne vulgaris in a patient in need thereof, the method comprising administering to the patient a therapeutically effective amount of a compound having formula (I), or aziridine derivatives, analogs, or pharmaceutically acceptable salts thereof: where R is a hydrogen or —C(O)—Z, and Z is a branched or straight chain $C_1$-$C_6$ alkyl group; X is a hydrogen, hydroxyl, or halogen; and Y is a branched or straight chain $C_1$-$C_6$ alkyl group.

Embodiment 30

A method of treating androgenetic alopecia in a patient in need thereof, the method comprising administering to the patient a therapeutically effective amount of a compound having formula (I), or aziridine derivatives, analogs, or pharmaceutically acceptable salts thereof: where R is a hydrogen or —C(O)—Z, and Z is a branched or straight chain $C_1$-$C_6$ alkyl group; X is a hydrogen, hydroxyl, or halogen; and Y is a branched or straight chain $C_1$-$C_6$ alkyl group.

EXAMPLES

The following examples are illustrative and are not intended to limit the scope of the claimed subject matter.

Example I. Synthesis of CpdA 2-(4-acetoxyphenyl)-2-chloro-N-methyl-ethylammonium chloride (CpdA) was synthesized from (±)-Synephrine and acetyl chloride in glacial acetic acid by a modification of the original method of Bretschneider et al., Monatschefte fuer Chemie (in German) 1948; 78:82-116, which is incorporated by reference in its entirety.

Example II. Compound a Inhibits the Growth and the Survival of Cancer Cells

A. Background

Androgens are causatively involved in the development of different diseases and disorders in target organs and tissues such as prostate and skin. They are major etiological factors for the development of benign prostatic hyperplasia (BPH), and the development and progression of hormone-responsive prostate cancer (Feldman et al., Heinlein et al., and Bullock et al.). Skin and hair androgen-dependent disorders/diseases include acne vulgaris and androgenetic alopecia-mail pattern hair loss (Clarke et al. and Kaufman et al.). Currently, anti-androgens are extensively used for the treatment of prostate cancer, BPH, androgenetic alopecia, and acne (Feldman et al., Heinlein et al., Clarke et al., Kaufman et al., and Bullock et al.). There is evidence that inflammation plays an important role in the development of many androgen-dependent diseases (Mahé et al., Clarke et al., Bullock et al., Kramer et al., Sutcliffe et al., and Haverkamp et al.). Glucocorticoid hormones that act via glucocorticoid receptor (GR) are among the most potent agents to treat inflammation. Thus, the multi-target (AR/GR) steroid receptor modulators that act as anti-inflammatory anti-androgens may be much more effective for the treatment of many androgen-dependent diseases and disorders than pure anti-androgens.

2-(4-acetoxyphenyl)-2-chloro-N-methylethyl-ammonium chloride, also called Compound A (CpdA) is a stable analog of an aziridine precursor from the African shrub *Salsola tuberculatiformis* Botschantzev. Recent studies show that CpdA interacts with both AR and GR in a unique way: it inhibits AR function and strongly enhances the anti-inflammatory function of GR (De Bosscher et al. 2005, Tanner et al.). CpdA has been proposed for clinical use as an anti-inflammatory drug with the reduced side effects. The potential of CpdA as anti-inflammatory anti-androgen for the treatment of PC, BPH, acne vulgaris and androgenetic alopecia has never been evaluated.

The results presented here suggest that CpdA indeed acts as a multi-steroidal receptor modulator. It shares binding cavities in AR and GR ligand-binding domains with corresponding hormones, and forms hydrogen (H)-bonds with the same amino acids that are involved in H-bond formation during steroid binding. CpdA induces nuclear translocation of both AR and GR, but inhibits AR-DNA binding and AR function. On the other hand, CpdA induces GR-mediated transrepression measured by blockage of pro-inflammatory transcription factors NF-κB and AP-1. These studies also demonstrate that CpdA induces strong growth inhibitory and pro-apoptotic effects in numerous human malignant cell lines (including androgen-dependent and androgen-independent prostate carcinoma cells, melanoma cells, and multiple myeloma cells), and that the cytotoxic effect of CpdA is dependent on GR, AR, or both. Thus, these data suggest that CpdA is a unique multi-target steroid receptor phyto-modulator that acts as anti-inflammatory anti-androgen, and could be used for the treatment of patients with cancer, BPH, acne, androgenetic alopecia, and other androgen-dependent or androgen-independent diseases which may include an inflammatory component.

1. Steroid Hormone Receptors.

Steroid hormone receptors such as androgen receptor (AR) or glucocorticoid receptor (GR) are transcription factors that regulate gene expression. In non-activated cells each receptor resides in the cytoplasm in a complex with chaperone proteins. Upon activation by corresponding steroid hormones (GR is activated by glucocorticoids; AR is activated by androgens) receptors dissociate from the chaperones, form homo-dimers and enter the nucleus (De Bosscher et al. 2003, McKay et al., and Schacke et al. 2002). There are two major mechanisms of gene regulation by GR and AR. One is activation of gene expression, called transactivation. It requires binding of AR/AR or GR/GR diners to the regulatory sequences in the promoters of corresponding target genes (De Bosscher et al. 2003, McKay et al., and Schacke et al. 2002,). The alternative mechanism of gene regulation is transrepression. This negative regulation of gene activity is chiefly mediated via inhibition of other transcription factors by steroid hormone receptors dissociated from the chaperones. The negative regulation of gene expression by GR is better studied. It was shown that GR interacts with numerous transcription factors including leading pro-inflammatory factors such as NF-κB and AP-1. This interaction results in blocking of NF-κB and AP-1 activity (De Bosscher et al. 2003, Yemelyanov et al., and McKay et al.). Gene transrepression by GR appears to be critical for the therapeutic anti-inflammatory effects of glucocorticoids (De Bosscher et al. 2003, Schacke et al. 2002). Other recent work clearly indicates that tumor suppressor effects of GR/glucocorticoids also involve gene transrepression (Yemelyanov et al., and Chebotaev et al.). Glucocorticoids are notorious for their side effects (Schacke et al. 2002). It was shown that in contrast to therapeutic effects of glucocorticoids their undesirable side effects are mostly mediated via gene activation (Schacke et al. 2002). Thus, GR ligands that specifically activate transrepression may hold a great potential as anti-inflammatory drugs with reduced side effects.

2. Androgen-Dependent Diseases of Prostate.

Androgens and AR promote the development of BPH and the development and progression of hormone-dependent prostate cancer (Feldman et al., and Heinlein et al.). Further, it became recently apparent that inflammation contributes to the development of both BPH and PC prostate growth (Bullock et al., Kramer et al., Sutcliffe et al., Haverkamp et al., and Nelson). It has been shown that signaling mediated by GR, especially GR transrepression, inhibits PC cell growth and plays a tumor suppressor role in prostate (Dondi et al., Nishimura et al., Smith et al., Yano et al., and Yemelyanov et al.). In addition, GR ligands may prevent the development of BPH and PC via inhibition of inflammation in prostate. As activation of AR and GR have opposite effect on prostate cells, the multi-target steroid receptor modulators that act as anti-inflammatory anti-androgens may be very effective for BPH and PC therapy.

3. Androgen-Dependent Diseases of Skin and Hair

Acne vulgaris. The etiological factors for acne include increased sebum production, infection and inflammation. Androgens play an important role in the pathophysiology of acne as they specifically stimulate the production of sebum and increase the size of sebaceous glands (Clarke et al.). Cells in the basal layer of the sebaceous gland express AR, and can produce androgens locally (Clarke et al.). It is also known that pro-inflammatory cytokines including IL-1 are involved in the development of acne (Clarke et al.).

Androgenetic Alopecia. Androgens are very potent modulators of hair growth: in androgen-sensitive males hair follicles of the scalp become smaller under the influence of androgens (miniaturization) leading to the typical changes of androgenetic alopecia (Kaufman et al). The scalp of predisposed individuals exhibits high levels of androgen DHT, and increased expression of the AR. Conversion of testosterone to DHT and activation of androgen-responsive genes by AR within the dermal papilla of hair follicle plays a central role, while androgen-regulated factors deriving from dermal papilla cells are believed to influence growth of other components of the hair follicle (Kaufman et al.). In addition, the sustained microscopic follicular inflammation is considered a possible cofactor in the complex etiology of alopecia (Trueb, 2000).

Treatment. Anti-androgens and finasteride—an inhibitor of 5-alpha-reductase that converts testosterone to more potent androgen DHT, are currently used for the treatment of both listed above androgen-dependent skin disorders (Clarke et al., Trueb et al., and Kaufman et al.). Taking into consideration the role of inflammation in the development of acne and androgenetic alopecia, the multi-target steroid receptor modulators that act as anti-inflammatory anti-androgens may be very effective for acne and androgenetic alopecia treatment.

4. Compound A—a Phyto-Modulator of Steroid Hormone Receptors 2-(4-acetoxyphenyl)-2-chloro-N-methyl-ethylammonium chloride, also called Compound A (CpdA), is a synthetic analog of the highly liable aziridine precursor found in the African shrub *Salsola tuberculatiformis* Botschantzev (Swart et al. 2003). The aqueous extract of this plant has been used by Bushmen women as a traditional medicine (Swart et al. 2003). It has been shown recently that CpdA directly interacts with steroid receptors AR and GR. Importantly; it inhibits AR function and strongly enhances the anti-inflammatory function of GR (De Bosscher et al. 2005, Tanner et al.). CpdA, similar to well-characterized anti-androgens, represses the activation of AR by inhibition of the androgen-dependent interaction between $NH_2$— and COOH-terminal domains of the AR (Tanner et al.). At the same time, CpdA acts GR ligand: it competes with glucocorticoids for GR binding and induces GR translocation into the nucleus (De Bosscher et al. 2005). As mentioned above, there are two major mechanisms underlying gene regulation by GR: positive regulation (transactivation) and negative regulation (transrepression) that is mediated via negative interaction between GR and other transcription factors (De Bosscher et al. 2003, Schacke et al. 2002, Yemelyanov et al.). It is well understood that many therapeutic anti-inflammatory effects of glucocorticoids are mediated via gene transrepression. It was shown that CpdA possesses the properties of the "dissociated" GR ligand that specifically induces GR-mediated transrepression (De Bosscher et al. 2005, Tanner et al.). Furthermore, in in vivo experiments, CpdA acts as a strong anti-inflammatory compound with reduced side effects (De Bosscher et al. 2005).

Using virtual docking analysis, CpdA was found to potentially share binding cavities in AR and GR ligand-binding domains with corresponding hormones, and to potentially form H-bonds with the same amino acids that are involved in H-bond formation during steroid binding. Thus, CpdA has a unique combination of properties and acts as anti-inflammatory anti-androgen. Further, using numerous human tumor cell lines including prostate carcinoma, melanoma, and multiple myeloma cells, CpdA was shown to exhibit strong growth inhibitory and pro-apoptotic effects in tumor cells, and that this effect is GR/AR-dependent. Overall, this data suggests that CpdA is a unique dual-target steroid receptor modulator that has a high potential for therapy of androgen-dependent diseases and disorders that have an inflammatory component.

B. Methods and Results

1. Virtual docking analysis of CpdA binding to ligand binding domains (LBD) of steroid hormone receptors The chemical structure of CpdA significantly differs from most known AR/GR antagonists and GR dissociated ligands. Thus, CpdA was evaluated as a ligand of these steroid hormone receptors using virtual docking (FIG. 1). For analysis, recently published crystal structures of ligand binding domains (LBD) of AR and GR available from the Protein Bank Database website and a virtual docking software package (Molegro, Aarhus Denmark) were employed.

Structural biology modeling predicts that CpdA shares binding cavities within LBDs of GR and AR. The results predicted that CpdA could bind to LBDs of both AR and GR at the binding pockets of natural steroid ligands: glucocorticoid dexamethasone (Dex) and androgen 5-alpha-dihydrotestosterone (DHT).

Structural biology modeling also predicts that CpdA and steroid hormones form H-bonds with the same amino acids lining LBD cavities in steroid receptors. Structural analysis predicts that CpdA will form H-bonds (Hydrogen bonds) with the same amino acids that are involved in H-bond formation during steroid binding (Asn564 and Arg611 in GR; Asn705 and Arg752 in AR ligand binding domains). Overall these virtual docking data clearly indicate that CpdA indeed acts as a ligand for both GR and AR.

2. Effect of CpdA on AR Function

Figure 2:
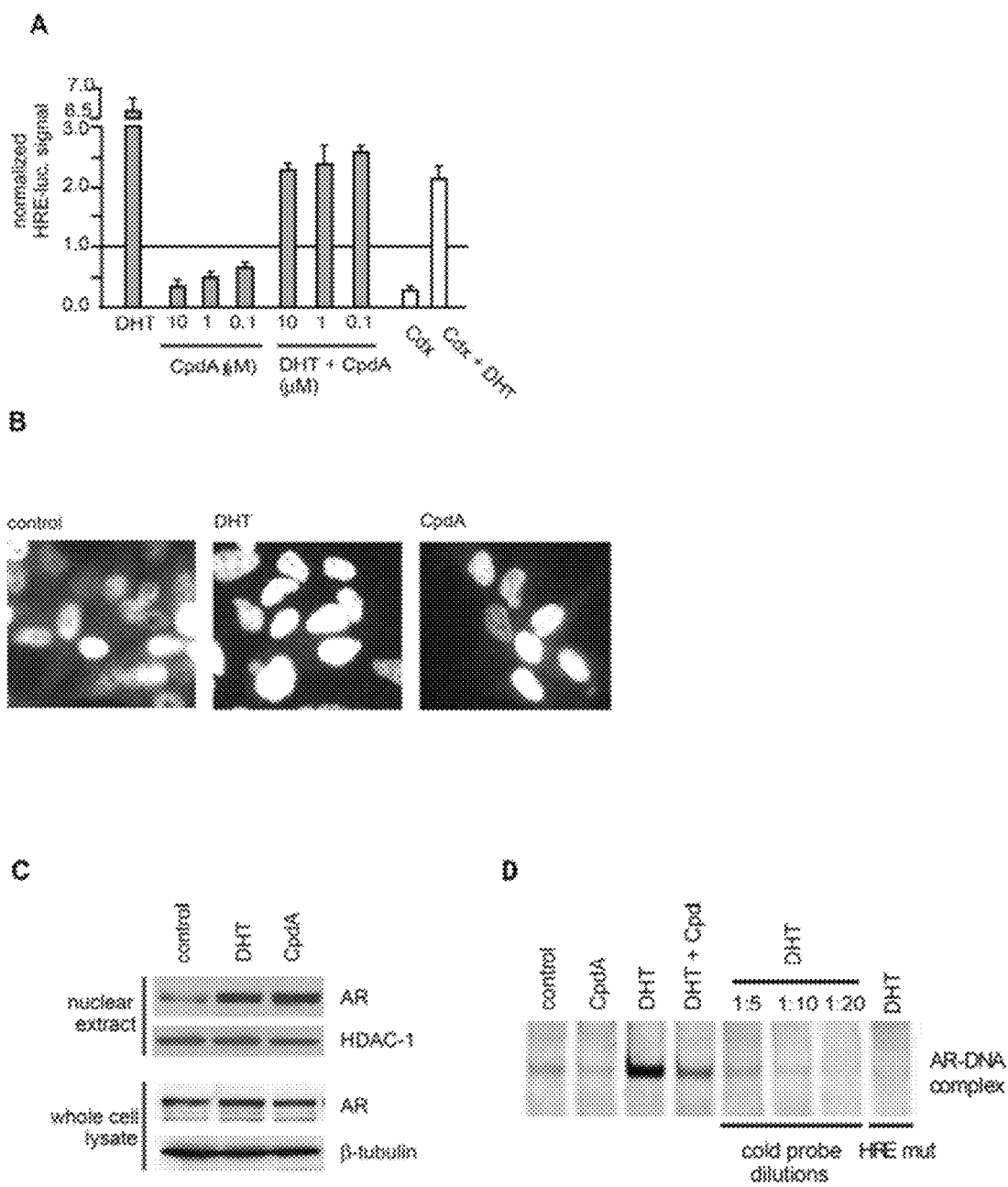
FIG. 2. CpdA inhibits AR function in LNCaP cells. A. Luciferase reporter assay in LNCaP cells transfected by lipofection with ARE.Luc reporter (Panomics, Fremont, Calif.). After transfection, cells were treated for 24 hours with DMSO, CpdA ($2 \times 10^{-6}$ M), DHT ($10^{-7}$ M) or the anti-androgen Casodex (Cdx, $10^{-7}$ M). B. Nuclear localization of AR was assessed by immunofluorescence. C. & D. Whole-cell and protein nuclear extracts from LNCaP cells treated with CpdA and DHT for 16 hours were analyzed by Western blotting and EMSA. HDAC-1 and β-tubulin were used as protein loading controls. For EMSA, native and mutated ARE were labeled with $\gamma$-$P^{32}$-ATP. CpdA treatment was observed to induce nuclear translocation of AR but to reduce its DNA-binding and transcriptional activity.

It was shown that CpdA inhibits AR function in model cells (Tanner et al.). To evaluate the effect of CpdA on AR function in epithelial cells expressing endogenous AR, LNCaP prostate cells were studied using several methods including: (i) Western blot analysis and immunofluorescence to detect CpdA effect on AR transport to the nucleus; (ii) EMSA to assess the effect of CpdA on AR-DNA binding; and (iii) dual Luciferase assay to evaluate CpdA effect on AR transcriptional activity (FIG. 2).

a. CpdA Induces AR Nuclear Translocation

Western blot analysis and immunostaining were utilized to study AR nuclear translocation. Similarly to androgen DHT (5-alpha-dihydrotestosterone), CpdA was found to induce AR nuclear translocation (FIG. 2B, 2C).

b. CpdA Inhibits AR-DNA Binding and AR Transcriptional Activity

To study AR function, electrophoretic mobility shift assay (EMSA) was utilized along with dual Luciferase assay using an androgen-responsive PSA.Luciferase reporter. CpdA was found to constitutively inhibit AR DNA binding and especially DHT-induced AR DNA binding (FIG. 2D). The AR DNA binding was specific and did not occur an oligonucleotide with a mutated androgen-responsive element (ARE, called HREmut in the FIG. 2D, last lane in FIG. 2D) was utilized.

CpdA also inhibited basal and DHT-induced transcriptional activity of AR in LNCaP cells (FIG. 2A). These results extended the previous finding on the inhibitory effect of CpdA on AR function in model cells transiently transfected with AR (Tanner et al.).

3. Effect of CpdA on GR Function

Figure 3:
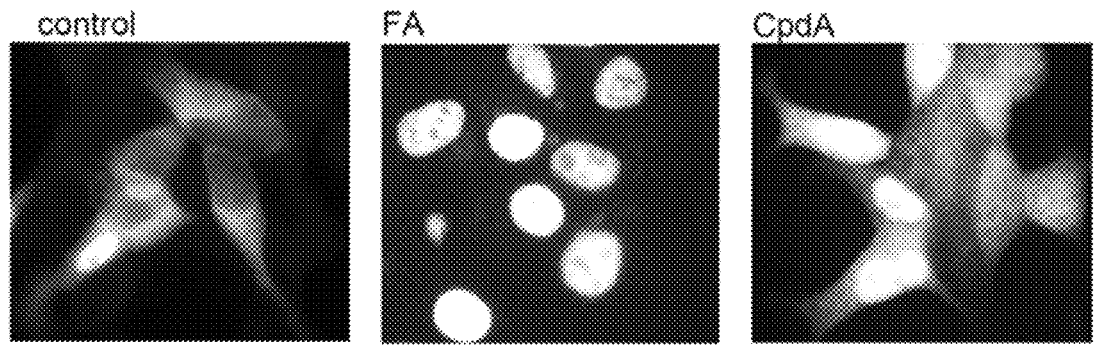
FIG. 3. Effect of CpdA on GR function in PC cells. A. & B. CpdA-activated GR nuclear translocation. Cells were treated with CpdA, glucocorticoid FA, or anti-glucocorticoid RU486. Panel A (immunofluorescence). Panel B (Western blotting of nuclear protein using HDAC-1 and β-tubulin as protein loading controls). C. CpdA decreased GR-DNA binding (EMSA, nuclear proteins). LNCaP-GR cells were treated with 0.01% DMSO (control), Dex ($10^{-7}$ M) or CpdA ($10^{-5}$ M) for 4 hours. D. & E. CpdA effect on GR function. PC cells were transiently transfected with TAT.Luc (D) or κB.Luc (E), and control Renilla Luciferase reporters, treated with Dex ($10^{-6}$ M) or CpdA ($10^{-5}$ M) for 24 hours. For activation of NF-κB, cells were co-transfected with CMV.IKKβ plasmid (in panel E). Reporter activity was assessed by dual Luciferase assay and presented as factor of change. CpdA was observed to induce GR nuclear translocation; to inhibit DNA binding and GR transactivation; and to induce GR transrepression.
Figure 3:
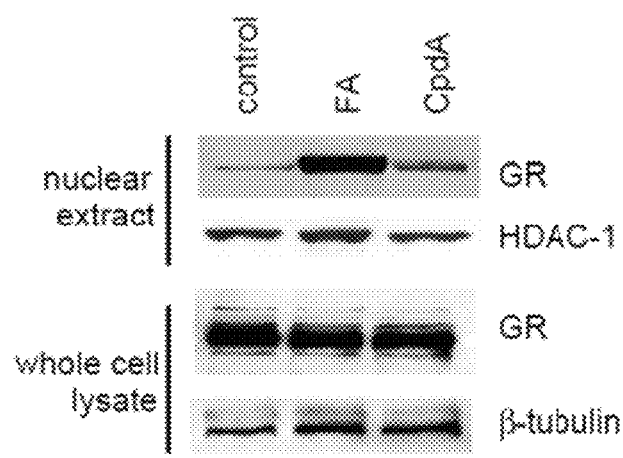
Figure 3:
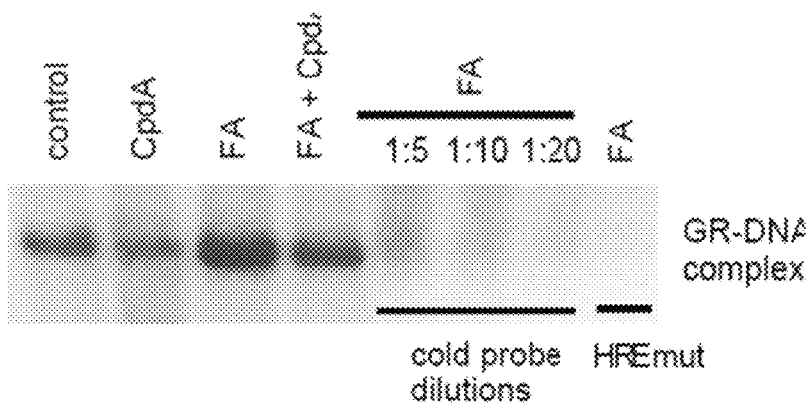
Figure 4:
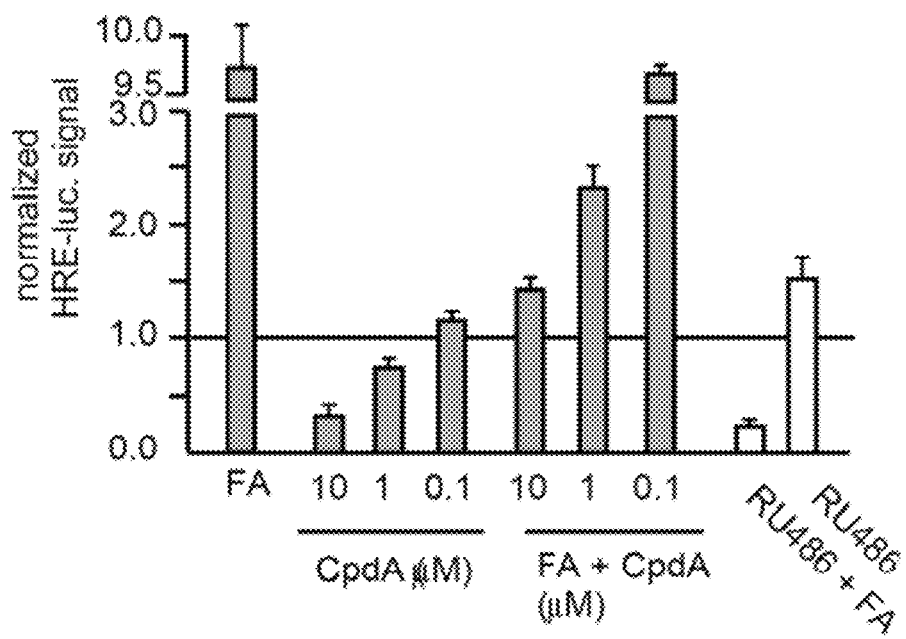
FIG. 4. CpdA effect on GR function. A. & B. PC cells were transiently transfected with TAT.Luc (A) or κB.Luc (B), and control Renilla Luciferase reporters. Cells were treated with Dex ($10^{-6}$ M) and CpdA ($10^{-5}$ M) for 24 hours. For activation of NF-κB (as shown in panel B), cells were co-transfected with CMV.IKKβ plasmid. Reporter activity was assessed by dual Luciferase assay and presented as factor of change. CpdA was observed to induce GR nuclear translocation; to inhibit DNA binding and GR transactivation; and to induce GR transrepression.
Figure 4:
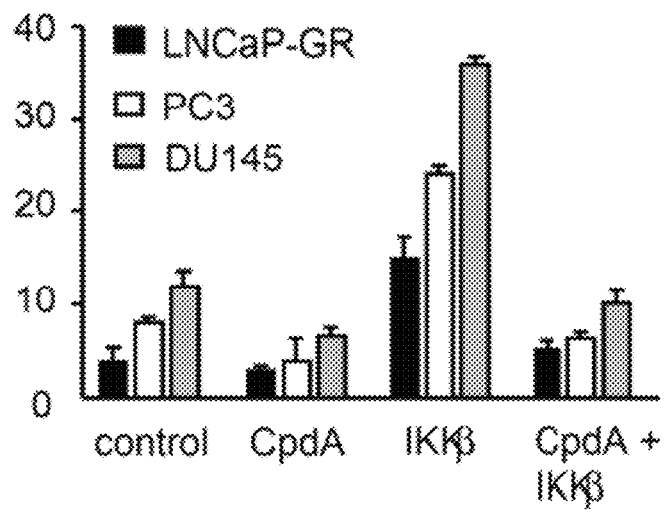

It was shown that CpdA acts in the model cells as dissociated ligand for GR that specifically induced GR transrepression activity (De Bosscher et al. 2005). To evaluate the effect of CpdA on GR function in epithelial cells expressing endogenous GR, several prostate cell lines were studied using several methods including: (i) Western blot analysis and immunofluorescence to detect CpdA effect on GR transport to the nucleus; (ii) EMSA to assess the effect of CpdA on GR-DNA binding; and (iii) dual Luciferase assay to evaluate CpdA effect on GR transactivation and GR transrepression activities (FIG. 3 & FIG. 4). For the last group of assays, transient transfections were performed using a TAT. Luciferase reporter, which is positively regulated by glucocorticoids, and a NF-κB.Luciferase reporter, which is negatively regulated by glucocorticoids (FIG. 4).

a. CpdA Induces GR Nuclear Translocation

Using Western blotting and immunofluorescence (FIGS. 3A and B), CpdA was found to induce GR nuclear import in LNCaP-GR cells. Even though the effect of CpdA on GR nuclear translocation was weaker than the effect of synthetic glucocorticoid fluocinolone acetonide (FA), this result suggests that CpdA acts as GR ligand.

b. CpdA Inhibits GR-DNA Binding and GR Transactivation

Using an electrophoretic mobility shift assay (EMSA), CpdA was shown to constitutively inhibit glucocorticoid-induced GR-DNA binding in LNCaP-GR cells (FIG. 3C). The GR-DNA binding was specific and did not occur when an oligonucleotide with a mutated glucocorticoid-responsive element (HRE mut, last lane in FIG. 3C) was utilized.

Using a dual Luciferase assay, CpdA was found to inhibit GR transcriptional activation in LNCaP-GR cells and other prostate cells such as DU145 and PC3 cells (FIG. 4 and data not shown), even though CpdA induced GR nuclear translocation (see above). At the same time, glucocorticoid FA induced TAT.Luc reporter activity in PC cells by 10-15 folds (FIG. 4A, first bar from the left).

c. CpdA Induces GR Transrepression Activity

CpdA strongly inhibited the function of NF-κB factor in all studied prostate cells (FIG. 4B). In the studied prostate cells, CpdA inhibited both basal and especially induced NF-κB activity (for NF-κB induction PC cells were transfected with IKKβ, an up-stream activating kinase). The negative interaction between GR and NF-κB transcription factors is a very important mode of GR action, and NF-κB protein p65 is a well defined GR "partner" whose activity is inhibited by GR/glucocorticoids (De Bosscher et al. 2003, Schacke et al. 2002, Yemelyanov et al.). Overall, these results confirmed that CpdA acts as a selective GR modulator that preferentially activates GR gene transrepression in prostate cells with endogenous and transfected GR.

4. CpdA Inhibits Prostate Carcinoma Cell Growth and Decreases Their Viability

Figure 5:
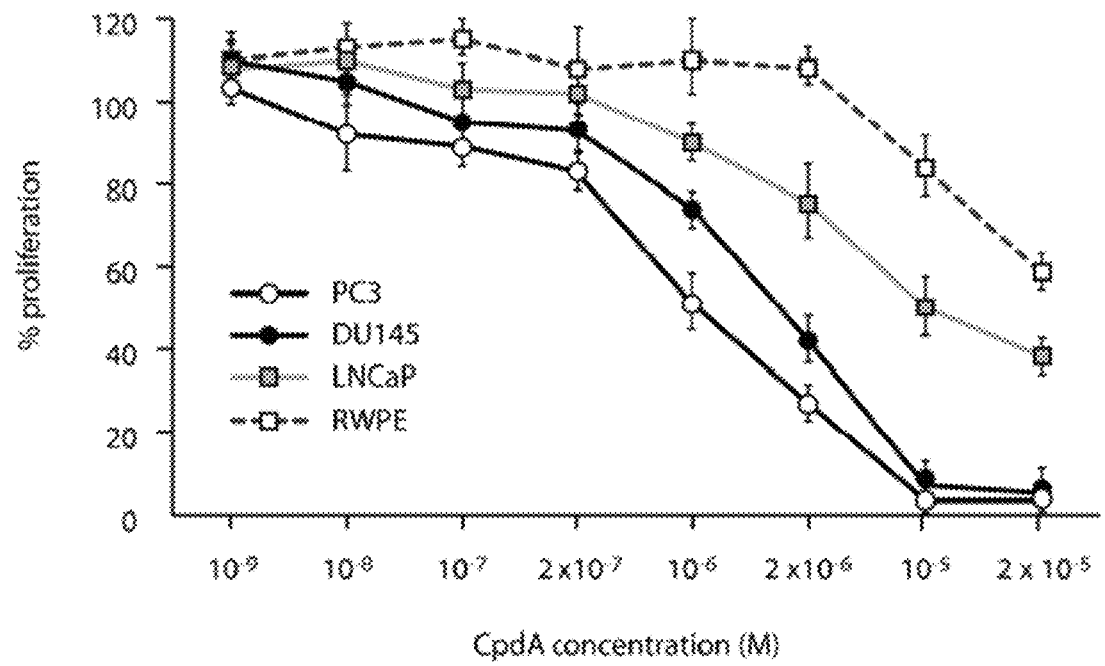
FIG. 5. Concentration-dependent effect of CpdA on the growth of prostate cells and PC cell lines. A. Non-transformed prostate cells PWR-1E and PC cells (LNCaP, DU145, and PC3 cells) were plated onto twelve plates ($10^4$ cells/well, each experimental group consisting of three wells), and treated with 0.01% DMSO (control) or CpdA ($10^{-9}$ M–$2 \times 10^{-5}$ M) for 72 hours. Cell number per well was determined by counting in a hemocytometer. The number of cells treated with CpdA is presented as a percentage of the average number of corresponding cells treated with vehicle only. The results of one representative experiment are presented as mean±S.D. for each experimental group (three wells/group). CpdA was observed to strongly inhibit the growth of the highly malignant cell lines DU145 and PC3. B. Experiments were performed as in panel A, except using CpdA ($10^{-6}$ M–$10^{-5}$ M). CpdA was observed to strongly inhibit the growth of the highly malignant cell lines DU145 and PC3.
Figure 5:
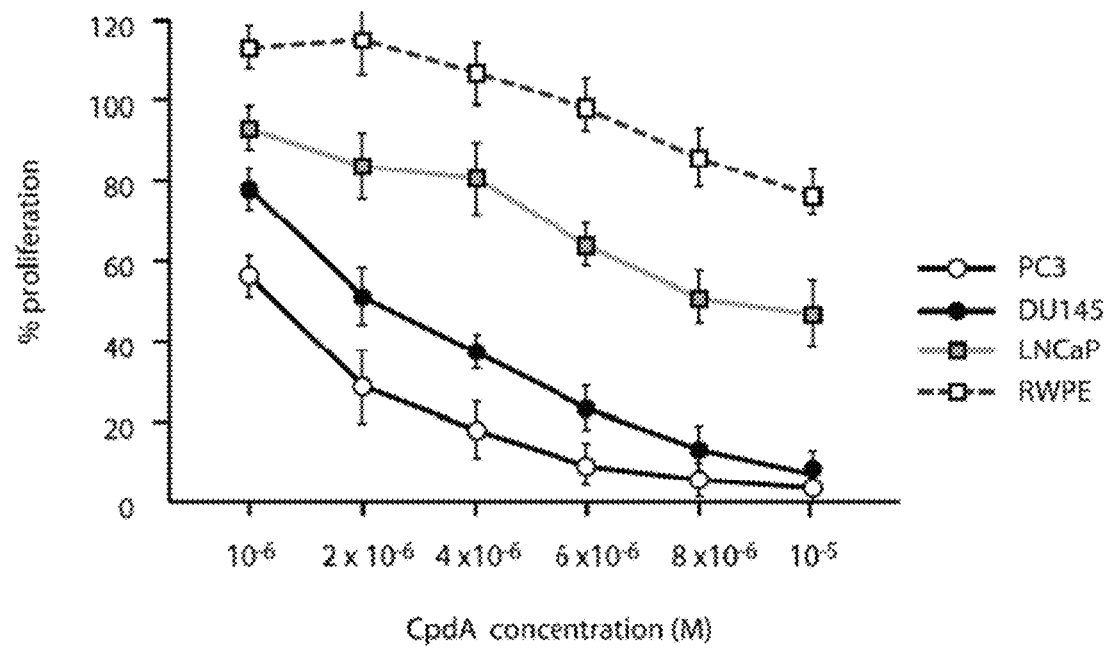

The effect of CpdA on tumor cells has never been studied. The effect of CpdA on growth and viability of prostate cancer cells was evaluated in vitro. In particular, the effect of CpdA on the growth of androgen-dependent LNCaP cells and two highly malignant androgen-independent cell lines DU145 and PC3 (FIG. 5 & FIG. 6) was studied. As a control, the effect of CpdA on the growth of non-transformed prostate cells PWR-1E (RWPE in FIG. 5) was studied.

a. CpdA is a Strong Inhibitor of PC Cell Growth

The effect of CpdA on PC cell growth using dose-effect and time-effect curves was assessed. Strong cytostatic effect of CpdA was observed at the concentration range: $2 \times 10^{-6}$-$10^{-5}$ M (2–10 μM) (FIGS. 5A & 5B). Those concentrations of CpdA were used in previous studies to evaluate the effect of CpdA on steroid hormone receptors in model cells (De Bosscher et al. 2005, Tanner et al.).

Figure 6:
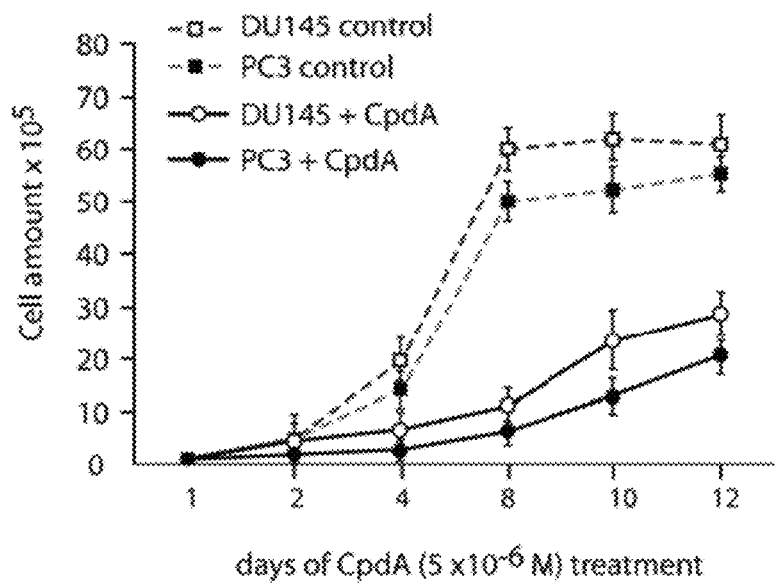
FIG. 6. Highly malignant PC cells are sensitive to the growth inhibitory effect of CpdA. A. & B. Non-transformed prostate cells PWR-1E and PC cells (LNCaP, DU145, and PC3 cells) were plated as described in FIG. 5 and treated with 0.01% DMSO (control) or CpdA ($5 \times 10^{-6}$ M) for 1-12 days. Cell number per well was determined by counting, and the absolute number of cells per well was determined as mean±S.D. for each experimental group (three wells/group). The androgen-independent PC cell lines DU145 and PC3 were observed to be highly sensitive to CpdA.
Figure 6:
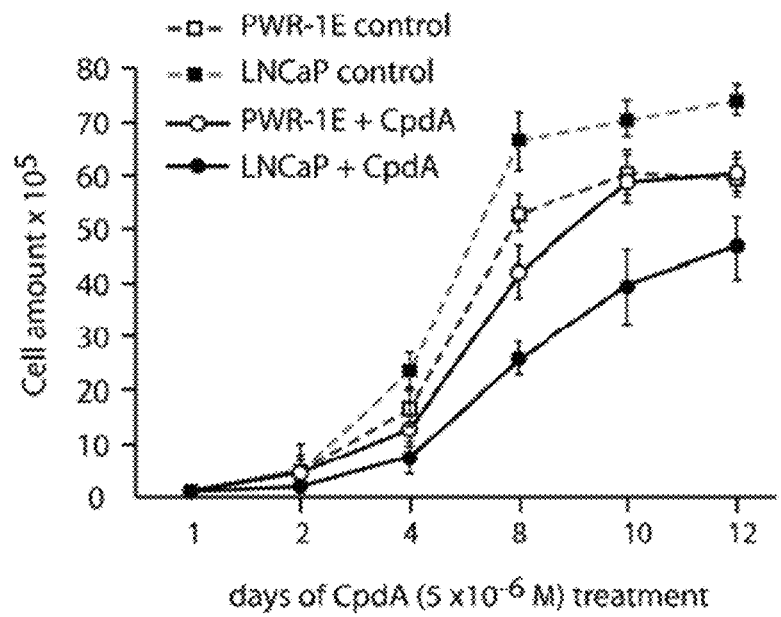

Time curves are presented in FIG. 6. As shown in FIGS. 6A & 6B, the treatment of prostate cells LNCaP, DU145 and PC3 cells with 5 μM CpdA resulted in strong growth inhibition. The highly malignant androgen-independent cell lines DU145 and PC3 appeared to be especially sensitive to CpdA: at the log phase (4-8 days in culture) growth was inhibited by ~60-65% in DU145 cells, and by 65-85% in PC3 cells compared to the respective vehicle-treated control cells (FIG. 6A). In contrast, the non-transformed PWR-1E cells appeared to be rather resistant to the growth inhibitory effect of CpdA at the tested range of concentrations (FIG. 6B).

b. CodA Reduces the Survival of Prostate Cancer Cells

Figure 7:
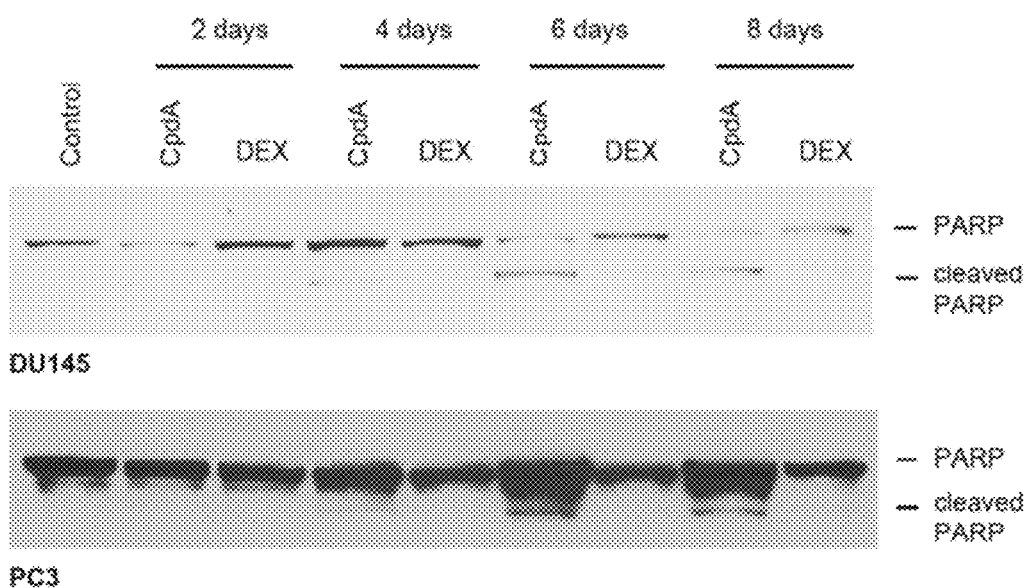
FIG. 7. CpdA induces apoptosis in prostate cells. A. PC3 and DU145 cells were treated for 1-8 days with DMSO (control), CpdA ($2 \times 10^{-6}$ M), or Dexamethasone ($10^{-6}$ M). Nuclear cell extracts were analyzed for PARP cleavage by Western blotting using anti-PARP antibody (Cell Signaling, Danvers, Mass.). B. To study prostate cell sensitization to apoptosis by CpdA, TNFα (10 ng/ml for 16 hours) was used to induce apoptosis after CpdA treatment. CpdA was observed to induce apoptosis after 6-8 days treatment, and CpdA was observed to sensitize cells to TNFα-induced apoptosis after a 2-day treatment.
Figure 7:
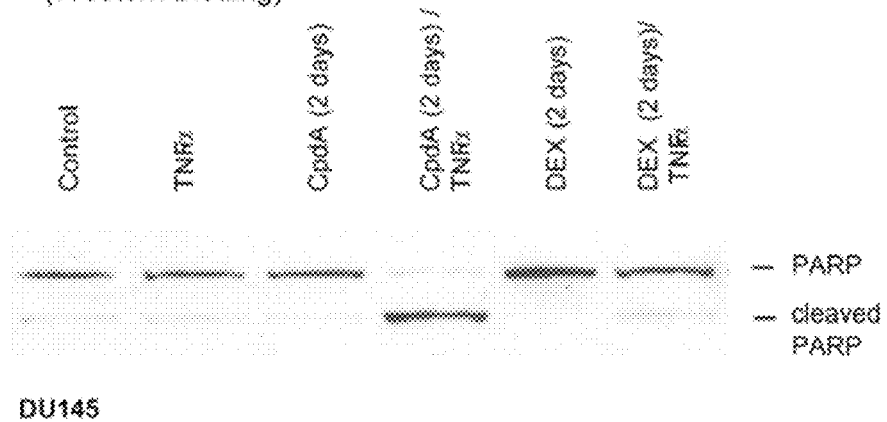

DU145 and PC3 cells are recognized as being resistant to multiple pro-apoptotic stimuli. As such, the effect of CpdA on sensitizing these cells to apoptosis was studied. The analysis of the poly-(ADP-ribose) polypeptide (PARP) cleavage (analysis of PARP cleavage is one of the standard assays to evaluate apoptosis) revealed that CpdA induced apoptosis after 6-8 day treatment and sensitized cells to TNFα-induced apoptosis after 2 day treatment (FIGS. 7A & 7B).

5. CpdA Inhibits Melanoma Cell Growth

Figure 8:
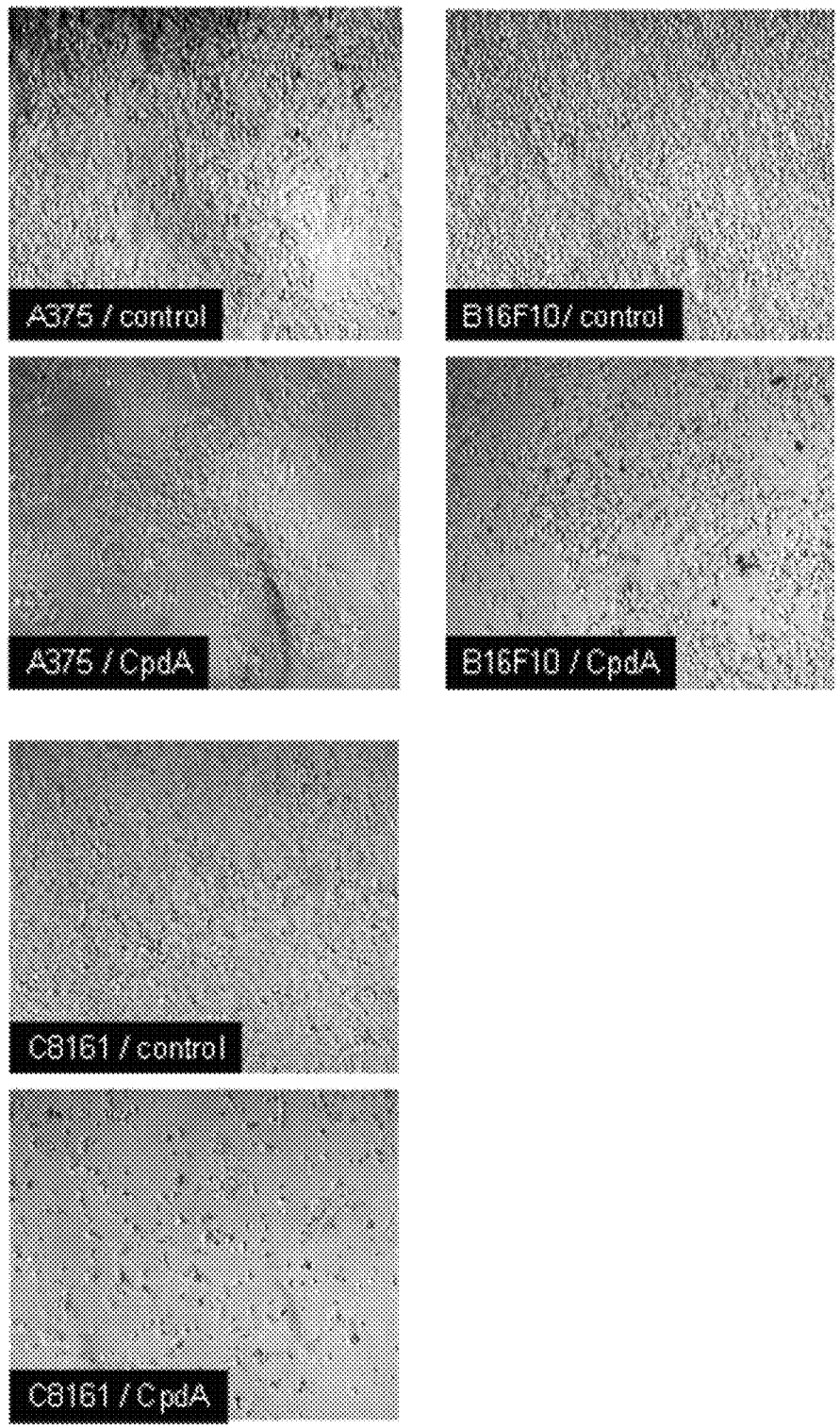
FIG. 8. Effect of CpdA on melanoma cell growth. Human melanoma cells (A375 and C8161) and mouse melanoma cells (B16F10) were plated onto twelve-well plates ($10^4$ cells/well, each experimental group consisting of three wells), and treated with 0.01% DMSO (control) or CpdA ($5 \times 10^{-6}$ M) for 72 hours. CpdA was observed to inhibit the growth of all three malignant cell lines.

To extend the finding that CpdA inhibits growth and survival of malignant cells, the effect of CpdA on melanoma cell growth was studied. As shown in FIG. 8, CpdA strongly inhibited growth of both mouse (B16F10) and human (A375 and C8161) melanoma cell lines.

6. Inhibition of PC Cell Growth by CpdA Depends on AR or GR Expression

Figure 9:
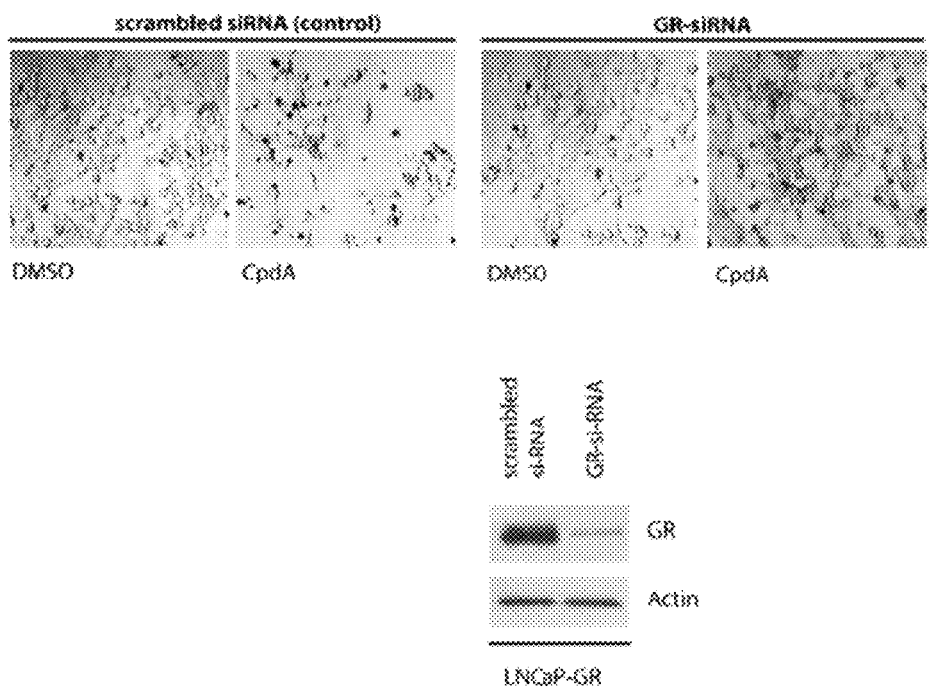
FIG. 9. GR is important for the CpdA-mediated cytostatic effect in PC3 and LnCAP-GR prostate cells. A. & B. PC cells were transfected with si-RNA against GR (GR-si-RNA) and inactive si-RNA-labeled with Cy3 as a negative control. Cells were treated with 0.01% DMSO (control) or CpdA ($2 \times 10^{-6}$ M) for 3 days and allowed to grow for another 3 days. Cells transfected with si-RNA against GR were observed to exhibit reduced sensitivity to the effect of CpdA. Western blot analysis of GR-expression in cells transfected with GR-si-RNA and control scrambled si-RNA. Actin was used as a protein loading control. GR-si-RNA was observed to strongly inhibit GR-expression in prostate cells.
Figure 9:
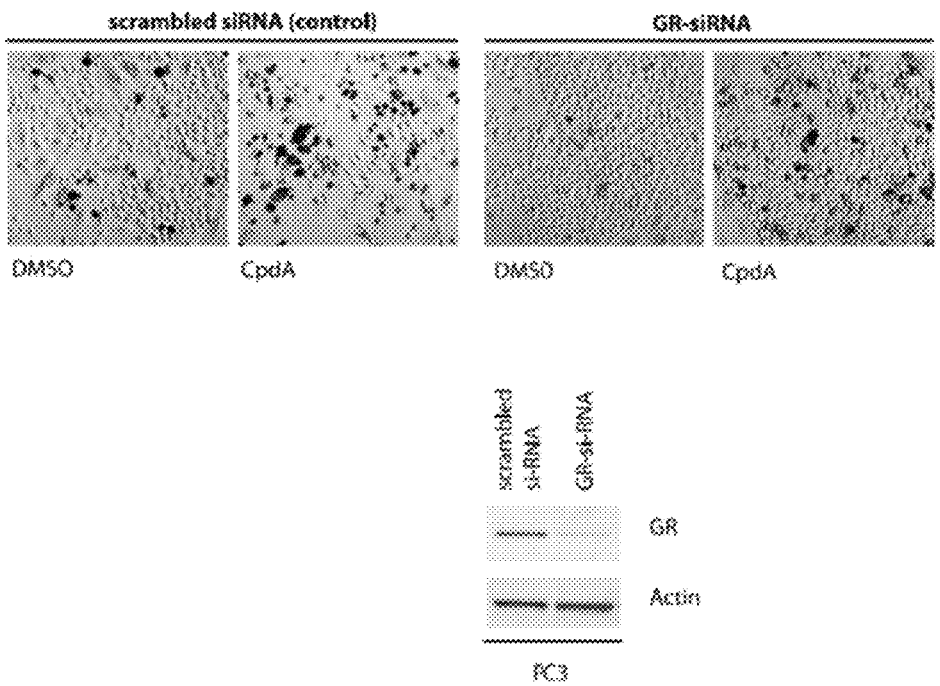

Prostate cells sensitive to CpdA have markedly different phenotype in terms of the expression of steroid hormone receptors. The most sensitive DU145 and PC3 cells express only GR, whereas LNCaP cells with moderate sensitivity to CpdA express only AR. To prove that GR plays an important role as a mediator of CpdA toxicity, two types of experiments were performed. First, the effect of CpdA on LNCaP cells stably infected with GR-expressing lentivirus was compared to the effect of CpdA on parental LNCaP cells. Importantly, LNCaP-GR cells appeared to be significantly more sensitive to growth inhibition by CpdA than control cells infected with empty virus both in monolayer and in colony-forming assay (data not shown). Second, using an siRNA approach, GR expression was inhibited by about 70-80% in PC3 and LNCaP-GR cells. As shown in FIG. 9, GR blockage resulted in a drastic loss of sensitivity to CpdA in both prostate cell types.

Figure 10:
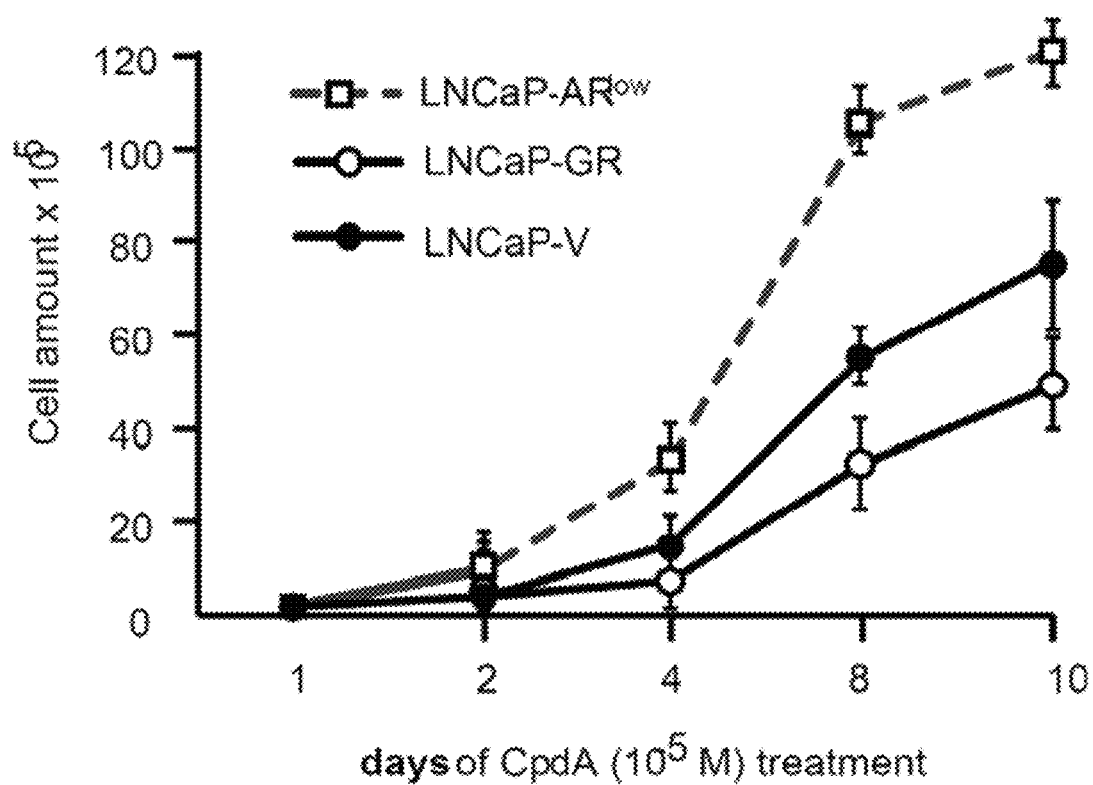
FIG. 10. AR is important for the CpdA-mediated cytostatic effect in prostate cells. An LNCaP cell clone with relative low AR-expression (LNCaP-AR$^{low}$), LNCaP-GR, and LNCaP-V (vector transfected) cells were treated with CpdA ($2\times10^{-6}$ M) for 1-10 days. Cell number was determined by counting, and the absolute number of cells per well was determined as mean±S.D. for each experimental group (three wells/group), LNCaP-AR$^{low}$ cells that do not express both AR and GR were observed to be almost completely resistant to CpdA.

To further study the role of AR in CpdA-mediated effects, an androgen-independent clone of LNCaP cells was derived from parental LNCaP cells during selection. This clone exhibited low AR expression and was called LNCaP-AR$^{low}$. As shown in FIG. 10, LNCaP-AR$^{low}$ cells that express low amounts of AR and no GR are resistant to CpdA mediated growth inhibition.

C. Conclusion

All together, these data suggest that CpdA acts as a ligand for both AR and GR. CpdA inhibits AR function and induces GR transrepression acting as unique anti-androgen with pro-inflammatory potential. This multi-target steroid receptor modulator has strong growth inhibitory and pro-apoptotic effects in different tumor cell cells. Its cytotoxic effect was AR-dependent, GR-dependent, or both AR- and GR-dependent. Overall these results indicate that CpdA could be used in the future for the treatment of cancer patients as well as for other patients having diseases and disorders associated with AR, GR, or both receptors.

Example III. Effect of CpdA on Human PC Cell Growth and Apoptosis In Vivo

PC3 cells readily form tumors when injected subcutaneously into athymic mice. PC3 cells are injected subcutaneously ($10^6$/cells/injection) into both flanks of forty athymic Cr1:CD1-Foxn1$^{nu}$ males (Charles River) as in (Nishimura K et al. J Natl Cancer Inst., 93(22):1739-1746 (2001)). Two days after injections mice are randomly divided into four groups (10 animals/group) and treated three times a week, for 8 weeks with: 1) CpdA (12.5 mg/kg, i.p.), 2) CpdA (12.5 mg/kg, s.c. peri-tumor injections), 3) 0.1% Ethanol in sterile saline buffer (vehicle control, i.p.); 4) 0.1% Ethanol in sterile saline buffer (vehicle control, s.c. peri-tumor injections). The CpdA at the proposed concentration has been tested in rodents and has been observed to exert a strong anti-inflammatory effect (De Bosscher et al. 2005, and Louw et al. 1999). In parallel with standard i.p. injections, subcutaneous injections at peri-tumor site are performed, as this route of drug delivery has been used successfully for inhibition of growth of human PC xenografts by glucocorticoids in previous work (Nishimura et al., and Yano et al.).

To assess the effect of CpdA on the growth of PC cells expressing AR, the analogous experiment is performed with LNCaP cells. LNCaP cells are injected subcutaneously ($10^6$/cells/injection) in matrigel into both flanks of forty athymic Cr1:CD1-Foxn1$^{nu}$ males as described previously (Lee et al.).

PC cell tumorigenicity is assessed by incidence and tumor growth curves. The tumor size is measured weekly with a slide caliper. At the completion of experiment, animals are injected with BrdU to measure proliferation of prostate cells, and sacrificed by $CO_2$ asphyxiation followed by cervical dislocation. Tumors and animal prostate are harvested, fixed in formalin and snap-frozen. Prostate is harvested from the animals treated with vehicle and CpdA systemically, via i.p. injections. The prostate lobes are separated under a dissection microscope, half of the lobes are frozen, the other half are fixed in formalin and embedded in paraffin en bloc (all prostate lobes separately). The effect of CpdA on GR and AR function in tumors and in prostate is analyzed by EMSA, Q-RT-PCR analysis and immunostaining for the expression of endogenous GR and AR-dependent genes (with the focus on CpdA-responsive genes revealed in the experiments proposed in Specific Aim 2). GR transrepression is assessed by the status of NF-κB ans AP-1 transcription factors as described (Yemelyanov et al.). The effect of CpdA on apoptosis in PC tumors is evaluated by TUNEL staining as described (Nelius et al.). Changes in angiogenesis are assessed by immunostaining of tumor tissues with endothelial marker CD31 as described (Nelius et al.).

The major outcome measure, on which sample size is computed, is the success rate of the implants. Assuming the success or failure of growth is independent in two sites of injection in one animal, 10 animals provide 20 sites. If 18 tumors succeed in the positive control group, the success rate is 90%. The experimental protocol provides 80% power to detect a 55% inhibition of growth in any given experimental group.

REFERENCES

Bretschneider et al., Monatschefte fuer Chemie (in German) 948; 78:82-116, which is incorporated by reference in its entirety.

Bullock T L and Andriole G L Jr. (2006) Emerging drug therapies for benign prostatic hyperplasia. Expert Opin Emerg Drugs. 11(1):111-123.

Chebotaev D, Yemelyanov A, Budunova I. The mechanisms of tumor suppressor effect of glucocorticoid receptor in skin. Mol Carcinog. 2007 August; 46(8):732-40.

Clarke S B, Nelson A M, George R E, Thiboutot D M. (2007) Pharmacologic modulation of sebaceous gland activity: mechanisms and clinical applications. Dermatol Clin. 25(2):137-146.

De Bosscher, K. Vanden Berghe, W., and Haegeman, G. (2003) The interplay between the glucocorticoid receptor and nuclear factor-kappaB or activator protein-1: molecular mechanisms for gene repression. Endocr Rev. 24, 488-522.

De Bosscher K, Vanden Berghe W, Beck I M, Van Molle W, Hennuyer N, Hapgood J, Libert C, Staels B, Louw A, Haegeman G. A. (2005) Fully dissociated compound of plant origin for inflammatory gene repression. Proc Natl Acad Sci USA. 102(44):15827-15832.

De Bosscher et al., published international application no. WO 01/45693, which is incorporated herein by reference in its entirety.

Dondi, D., Maggi, R., Scaccianoce, E., Martini, L., Motta, M., Poletti, A., (2001) Expression and role of functional glucocorticoid receptors in the human androgen-independent prostate cancer cell line, DU145. J Mol Endocrinol. 26(3): 185-191.

Feldman, B. J. and Feldman, D. (2001) The development of androgen-independent prostate cancer. Nat. Rev. Cancer, 1:34-45.

Haverkamp J, Charbonneau B, Ratliff T L. (2007) Prostate inflammation and its potential impact on prostate cancer: A current review. J Cell Biochem. October 22; [Epub ahead of print].

Heinlein, C. A., and Chang, C. (2004). Androgen receptor in prostate cancer. Endocrin Rev, 25: 276-308.

Kaufman K D. (2002) Androgens and alopecia. Mol Cell Endocrinol. 198:89-95.

Kramer G, Mitteregger D, Marberger M. (2007) Is benign prostatic hyperplasia (BPH) an immune inflammatory disease? Eur Urol. 51(5):1202-1216.

Lee C. et al. In vivo and in vitro approaches to study metastasis in human prostatic cancer. Cancer Metastasis Rev. (1):21-8 (1993) March 12).

Louw A., Swart P, Allie F. (2000). Influence of an aziridine precursor on the in vitro binding parameters of rat and ovine corticosteroid-binding globulin (CBG). Biochem Pharmacol. 59(2):167-75.

Louw A. and Swart, P. (1999) *Salsola tuberculatiformis* Botschantzev and an aziridine precursor analog mediate the in vivo increase in free corticosterone and decrease in corticosteroid-binding globulin in female Wistar rats. Endocrinology, 140(5): 2044-2053.

Louw A., Swart, P., de Kock S. S., and van der Merwe K. J. (1997) Mechanism for the stabilization in viva of the zairidine precursor 2-(4-acetoxyphenyl)-2-chloro-N-methylethyl-ammonium chloride by plasma proteins. Biochem Pharmacol 53:189-197.

Mahé Y F, Michelet J F, Billoni N, et al. (2000). Androgenetic alopecia and microinflammation. Int J Dermatol, 39(8):576-584.

McKay L I, Cidlowski J A. Molecular control of immune/inflammatory responses: interactions between nuclear factor-kappa B and steroid receptor-signaling pathways. Endocr Rev. 1999 August; 20(4):435-59.

Nelius et al. Androgen receptor targets NFkappaB and TSP1 to suppress prostate tumor growth in vivo. Internal. J. Cancer, 121(5):999-1008 (2007).

Nelson W G. (2007) Prostate cancer prevention. Curr Opin Urol. 17(3):157-167.

Nishimura, K., Nonomura, N., Satoh, E., Harada, Y., Nakayama, M., Tokizane, T., Fukui, T., Ono, Y., Inoue, H., Shin, M., Tsujimoto, Y., Takayama, H., Aozasa, K., Okuyama, A. (2001) Potential mechanism for the effects of dexamethasone on growth of androgen-independent prostate cancer. J Natl Cancer Inst. 93(22): 1739-1746.

Schacke, H., Docke, W. D., and Asadullah, K. (2002) Mechanisms involved in the side effects of glucocorticoids. Pharmacol Ther. 9: 23-43.

Schacke H, Berger M, Rehwinkel H, Asadullah K. Selective glucocorticoid receptor agonists (SEGRAs): novel ligands with an improved therapeutic index. Mol Cell Endocrinol. 2007 Sep. 15; 275(1-2):109-17.

Smith, R. G., Syms, A. J., Nag, A., Lerner, S., Norris, J. S. (1985) Mechanism of the glucocorticoid regulation of growth of the androgen-sensitive prostate-derived R3327H-G8-A1 tumor cell line. J Biol Chem. 260(23: 12454-1263.

Sutcliffe S, Platz E A. Inflammation in the etiology of prostate cancer: an epidemiologic perspective. Urol Oncol. 2007 May-June; 25(3):242-249.

Swart, P., Swart, A. C., Louw, A., van der Merwe, K. J. (2003) Biological activities of the shrub *Salsola tuberculatiformis* Botsch.: contraceptive or stress alleviator? BioEssays, 25(6): 612-619.

Swart P., van der Merwe K. J., Swart A. C., Todres P. C., Hofmeyr J. H. S. (1993) Inhibition of cytochrome P45011b by some naturally occurring acetophenones and plant extracts form the shrub *Salsola tuberculatiformis*. Planta Med 59:139-143.

Tanner, T. M., Verrijdt, G., Rombauts, W., Louw, A., Hapgood, J. P., Claessens, F. (2003). Anti-androgenic properties of Compound A, an analog of a non-steroidal plant compound. Mol Cell Endocrin, 201: 155-164.

Trueb R M. (2003) Is androgenetic alopecia a photoaggravated dermatosis? Dermatology, 207(4):343-348.

Van der Merwe K. J., de Kock S. S., Swart P. Fourie L. (1991) The application of mass spectrometry in the study of labile natural products. Biochem Soc Trans 19:432s.

Yano A, Fujii Y, Iwai A, Kawakami S, Kageyama Y, Kihara K. (2006). Glucocorticoids suppress tumor lymphangiogenesis of prostate cancer cells. Clin Cancer Res. 12(20): 6012-6017.

Yemelyanov A., Czwornog J., Chebotaev D., Karseladze A., Kulevitch E, Yang X, and Budunova I. (2006) Tumor suppressor activity of glucocorticoid receptor in the prostate. Oncogene, 26(13):1885-1896.

In the foregoing description, certain terms have been used for brevity, clearness, and understanding. No unnecessary limitations are to be implied therefrom beyond the requirement of the prior art because such terms are used for descriptive purposes and are intended to be broadly construed. The different compositions and method steps described herein may be used alone or in combination with other compositions and method steps. It is to be expected that various equivalents, alternatives and modifications are possible. Any disclosure of a Markush group is to be construed as an explicit disclosure of all members of the Markush group individually and all possible subgroups and combinations of the members. All of the references cited herein are incorporated by reference in their entireties.

We claim:

1. A method of inhibiting prostate cancer cell growth in a patient having androgen-independent prostate cancer, the method comprising administering to the patient a therapeutically effective amount of a compound or a pharmaceutically acceptable salt thereof, the compound having a formula:

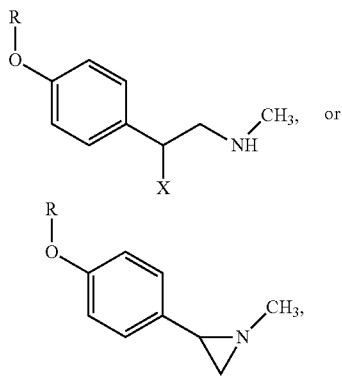

wherein R is hydrogen or —C(O)—CH$_3$, and X is a hydrogen or halogen.

2. The method of claim 1, further comprising administering an effective amount of a pro-apoptotic stimuli.

3. The method of claim 2, wherein the pro-apoptotic stimuli is selected from a group consisting of lonidamine, arsenite, PK 11195, LY294002, STI-571, PS-341, UCN-01, and flavopiridol.

4. The method of claim 1, further comprising assessing expression of a marker selected from the group consisting of hepsin, α-methylacyl-CoA racemase, and maspin in the patient prior to administering to the patient the therapeutically effective amount of the compound.

5. The method of claim 1, further comprising assessing expression of a marker selected from the group consisting of hepsin, α-methylacyl-CoA racemase, and maspin in the patient after administering to the patient the therapeutically effective amount of the compound.

6. A method of inhibiting prostate cancer cell growth in a patient having androgen-independent prostate cancer, the method comprising administering to the patient a therapeutically effective amount of 2-(4-acetoxyphenyl)-2-chloro-N-methyl-ethylammonium chloride or a pharmaceutically acceptable salt thereof.

7. The method of claim 6, further comprising administering an effective amount of a pro-apoptotic stimuli.

8. The method of claim 7, wherein the pro-apoptotic stimuli is selected from a group consisting of lonidamine, arsenite, PK 11195, LY294002, STI-571, PS-341, UCN-01, and flavopiridol.

9. The method of claim 6, further comprising assessing expression of a marker selected from the group consisting of hepsin, α-methylacyl-CoA racemase, and maspin in the patient prior to administering to the patient the therapeutically effective amount of 2-(4-acetoxyphenyl)-2-chloro-N-methyl-ethylammonium chloride.

10. The method of claim 6, further comprising assessing expression of a marker selected from the group consisting of hepsin, α-methylacyl-CoA racemase, and maspin in the patient after administering to the patient the therapeutically effective amount of 2-(4-acetoxyphenyl)-2-chloro-N-methyl-ethylammonium chloride.

* * * * *